(12) United States Patent
Vollmer et al.

(10) Patent No.: US 8,198,251 B2
(45) Date of Patent: Jun. 12, 2012

(54) COMBINATION MOTIF IMMUNE STIMULATORY OLIGONUCLEOTIDES WITH IMPROVED ACTIVITY

(75) Inventors: Jorg Vollmer, Dusseldorf (DE); Eugen Uhlmann, Glashuetten (DE); Arthur M. Krieg, Wellesley, MA (US); Douglas C. Hanson, Niantic, CT (US); Ulrike Samulowitz, Langenfeld (DE)

(73) Assignees: Coley Pharmaceutical GmbH, Düsseldorf (DE); Coley Pharmaceutical Group, Inc., Wellesley, MA (US); Pfizer Inc, New York, NY (US)

( * ) Notice: Subject to any disclaimer, the term of this patent is extended or adjusted under 35 U.S.C. 154(b) by 562 days.

(21) Appl. No.: 12/190,402

(22) Filed: Aug. 12, 2008

(65) Prior Publication Data

US 2009/0087446 A1     Apr. 2, 2009

Related U.S. Application Data

(60) Provisional application No. 60/964,477, filed on Aug. 13, 2007.

(51) Int. Cl.
*A61K 48/00* (2006.01)
(52) U.S. Cl. .................................................. 514/44 R
(58) Field of Classification Search .................. None
See application file for complete search history.

(56) References Cited

U.S. PATENT DOCUMENTS

2003/0148976 A1 * 8/2003 Krieg et al. ............... 514/44

FOREIGN PATENT DOCUMENTS

| WO | WO 03/015711 A2 | 2/2003 |
|---|---|---|
| WO | WO 2004/039829 A2 | 5/2004 |
| WO | WO 2004/087203 A2 | 10/2004 |
| WO | WO 2005/030259 A2 | 4/2005 |
| WO | WO 2005/042018 A2 | 5/2005 |
| WO | WO 2007/059041 A2 | 5/2007 |
| WO | WO 2008/068638 A2 | 6/2008 |

OTHER PUBLICATIONS

Bauer, S., et al., "Human TLR9 Confers Responsiveness to Bacterial DNA via Species-Specific CpG Motif Recognition", *PNAS*, 2001, 9237-9242, vol. 98, No. 16.
"CpG 7909 PF 3512676, PF-3512676", *Adis International, Drugs in R&D*, 2006, 312-316, vol. 7, No. 5.
Jurk, M., et al., "C-Class CpG ODN: Sequence Requirements and Characterization of Immunostimulatory Activities on mRNA level", *Immunobiology*, 2004, 141-154, vol. 209.

(Continued)

*Primary Examiner* — Oluwatosin Ogunbiyi
(74) *Attorney, Agent, or Firm* — Keith D. Hutchinson; Matthew J. Pugmire

(57) ABSTRACT

Immunostimulatory oligonucleotides, which contain a CpG immunostimulatory motif and a second motif that is capable of forming secondary structure, including duplex and higher order structures in vitro and in vivo, are disclosed. They include nucleic acids, or pharmaceutically acceptable salts thereof, having base sequences that include 5' TCGTCGTTTTCGGCGCGCGCCGT 3' (SEQ ID NO: 1), in which each C is unmethylated and 3' refers to the 3' end of the nucleic acid. The oligonucleotides activate B cells and NK cells and induce expression of type I interferon and interferon-γ. The oligonucleotides are useful for treating a variety of disorders and conditions, including allergy, asthma, infection, and cancer. In addition to their use as single agents and as combination therapies, the disclosed oligonucleotides are useful as adjuvants in vaccines.

1 Claim, 16 Drawing Sheets

OTHER PUBLICATIONS

Krieg, A. M., "Now I know my CpGs", *Trends in Microbiology*, 2001, 249-252, vol. 9, No. 6.

Krieg, A. M., "Therapeutic Potential of Toll-Like Receptor 9 Activation", *Nature Reviews Drug Discovery*, 2006, 471-484, vol. 5.

Latz, E., et al., "TLR9 Signals After Translocating From the ER to CpG DNA in the Lysosome", *Nature Immunology*, 2004, 190-198, vol. 5, No. 2.

Rutz, M., et al., "Toll-Like Receptor 9 Binds Single-Stranded CpG-DNA in a Sequence- and pH-Dependent Manner", *Eur. J. Immunology*, 2004, 2541-2550, vol. 34.

Vollmer, J., et al., "Characterization of Three CpG Oligodeoxynucleotide Classes with Distinct Immunostimulatory Activities", *Eur. J. Immunology*, 2004, 251-262, vol. 34.

International Search Report for PCT/IB2008/002102.

\* cited by examiner

```
                            SEQUENCE LISTING

<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 1
tcgtcgtttt cggcgcgcgc cgt                                              23

<210> SEQ ID NO 2
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: stabilized 5' internucleotide linkage
<220> FEATURE:
<221> NAME/KEY: misc_feature
<222> LOCATION: (3)..(3)
<223> OTHER INFORMATION: phosphodiester or phosphodiester-like 5'
      internucleotide linkage
<220> FEATURE:
<221> NAME/KEY: misc_feature
<222> LOCATION: (4)..(23)
<223> OTHER INFORMATION: stabilized 5' internucleotide linkage

<400> SEQUENCE: 2
tcgtcgtttt cggcgcgcgc cgt                                              23

<210> SEQ ID NO 3
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(23)
<223> OTHER INFORMATION: stabilized 5' internucleotide linkage

<400> SEQUENCE: 3
tcgtcgtttt cggcgcgcgc cgt                                              23

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(24)
<223> OTHER INFORMATION: phosphorothioate 5' internucleotide linkage

<400> SEQUENCE: 4
tcgtcgtttt gtcgttttgt cgtt                                             24
```

```
<210> SEQ ID NO 5
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(24)
<223> OTHER INFORMATION: phosphorothioate 5' internucleotide linkage

<400> SEQUENCE: 5
tgctgctttt gtgcttttgt gctt                                            24

<210> SEQ ID NO 6
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (24)..(27)
<223> OTHER INFORMATION: where each n is any nucleotide base and nnnn
      cannot be tttt

<400> SEQUENCE: 6
tcgtcgtttt cggcgcgcgc cgtnnnn                                         27
```

COMBINATION MOTIF IMMUNE STIMULATORY OLIGONUCLEOTIDES WITH IMPROVED ACTIVITY

CROSS-REFERENCE TO RELATED APPLICATION

This application claims the benefit of U.S. Provisional Application No. 60/964,477, filed Aug. 13, 2007, which is herein incorporated by reference.

BACKGROUND OF INVENTION

This invention relates to immunostimulatory nucleic acids, to compositions which contain them, and to the use of the immunostimulatory nucleic acids to treat various conditions and disorders, including cancer.

Several classes of immunostimulatory nucleic acids are known. Although many share an unmethylated cytosine-guanine (CpG) base sequence motif, they also possess structural differences that produce distinct immunostimulatory activities that characterize each class. See, e.g., Krieg, A M (2006) *Nature Reviews Drug Discovery* 5:471-84; Jurk, M et al. (2004) *Immunobiology* 209:141-54; Vollmer, J et al. (2004) *Eur. J. Immunol.* 34:251-62; Krieg, A M (2001) *Trends in Microbiology* 9:249-52. For example, A-class CpG oligodeoxyribonucleotides (ODN) typically include nuclease-resistant (stabilized) base sequences comprised of three or more consecutive guanines (poly-G motifs) at one or both ends, and a central region comprised of one or more CpG dinucleotides contained in a self-complementary palindrome. Members of A-class CpG ODN activate natural killer (NK) cells and induce interferon-alpha (INF-α) secretion from plasmacytoid dendritic cells (pDC). B-class CpG oligodeoxyribonucleotides typically include a stabilized non-palindromic nucleotide sequence, which comprises one or more CpG dinucleotides. In contrast to A-class ODN, B-class CpG oligodeoxyribonucleotides strongly activate B cells, but induce comparatively weaker INF-α secretion.

Commonly assigned, published international patent application WO 03/015711 (the '711 application) describes a third class of immunostimulatory nucleic acids. C-class CpG oligodeoxyribonucleotides typically include one or more CpG motifs, which are located within the 5'-region, and a palindromic sequence, which is located at or near the 3'-end. They exhibit immunostimulatory activity that is characteristic of both A-class and B-class CpG ODN, including induction of INF-α secretion and activation of NK cells. At similar concentrations, C-class oligodeoxyribonucleotides generally exhibit B cell activation that is greater than what is observed with A-class CpG ODN, but is less than what is typically seen with B-class CpG ODN.

Recent studies have shown that CpG oligodeoxyribonucleotides induce immunostimulatory activity through interaction with Toll-like receptor 9 (TLR9). See Rutz, M et al. (2004) *Eur. J. Immunol.* 34:2541-50; Bauer, S et al. (2001) *Proc. Nat'l Acad. Sci. USA* 98(16):9237-42; and Latz, E et al. (2004) *Nature Immunol.* 5(2):190-98. A number of TLR9 agonists have been evaluated, or are currently undergoing evaluation, in human clinical trials related to infectious diseases, cancer, and allergy-related disorders. See, e.g., Krieg, A M (2006) *Nature Reviews Drug Discovery* 5:471-84.

SUMMARY OF INVENTION

This invention relates to immunostimulatory oligonucleotides, including immunostimulatory CpG oligodeoxyribonucleotides, which may be used to treat diseases, conditions, and disorders associated with the immune system, including infectious diseases, cancer, and allergy-related disorders.

One aspect of the invention provides an immunostimulatory oligonucleotide having a base sequence comprising:

5' TCGTCGTTTTCGGCGCGCGCCGT 3',   (SEQ ID NO: 1)

in which each C in the base sequence is unmethylated and 3' in SEQ ID NO: 1 refers to the 3' end of the oligonucleotide.

The immunostimulatory oligonucleotide (SEQ ID NO: 1) may have a nuclease resistant backbone. For example, the oligonucleotide may have at least one internucleotide linkage which has a phosphate backbone modification, such as a phosphorothioate or phosphorodithioate modification. In some embodiments, every internucleotide linkage may have a phosphorothioate modification.

In addition, any of the aforementioned immunostimulatory oligonucleotides may have a base sequence in which 5' in SEQ ID NO: 1 refers to the 5' end of the immunostimulatory oligonucleotide.

In other embodiments, the immunostimulatory oligonucleotide (SEQ ID NO: 1) may have a length of 100 nucleotides or less.

Another aspect of the invention provides an immunostimulatory oligonucleotide having a base sequence comprising:

5' T*C_G*T*C*G*T*T*T*T*C*G*G*C*G*C*G*C*G*C*C*G*T 3',   (SEQ ID NO: 2)

in which each asterisk "*" in SEQ ID NO: 2 represents a stabilized internucleotide linkage and the underscore "_" in SEQ ID NO: 2 represents a phosphodiester or phosphodiester-like internucleotide linkage.

In some embodiments, the immunostimulatory oligonucleotide (SEQ ID NO: 2) may have a sequence in which 5' refers to the 5' end of the oligonucleotide and 3' refers to the 3' end of the oligonucleotide.

Another aspect of the invention provides an immunostimulatory oligonucleotide having a base sequence comprising:

5' T*C*G*T*C*G*T*T*T*T*C*G*G*C*G*C*G*C*G*C*C*G*T 3',   (SEQ ID NO: 3)

in which each asterisk "*" in SEQ ID NO: 3 represents a stabilized internucleotide linkage and the oligonucleotide is 23-26 nucleotides in length.

In some embodiments, the immunostimulatory oligonucleotide (SEQ ID NO: 2 or SEQ ID NO: 3) may have a sequence in which each asterisk "*" represents a phosphorothioate internucleotide linkage and the underscore "_" represents a phosphodiester internucleotide linkage. This includes immunostimulatory oligonucleotides in which the 5' and 3' notations in SEQ ID NO: 2 or SEQ ID NO: 3 refer to the 5' and 3' ends of the oligonucleotide, respectively.

Another aspect of the invention provides an immunostimulatory oligonucleotide having a base sequence comprising:

5' TCGTCGTTTTCGGCGCGCGCCGT 3',    (SEQ ID NO: 1)

in which each C in SEQ ID NO: 1 is unmethylated and the oligonucleotide is 23-26 nucleotides in length.

A further aspect of the invention provides an immunostimulatory oligonucleotide having a sequence comprising:

(SEQ ID NO: 6)
5' TCGTCGTTTTCGGCGCGCGCCGTX$_1$X$_2$X$_3$X$_4$ 3', in which each C is unmethylated, $X_1$, $X_2$, $X_3$, and $X_4$ are each independently a nucleotide base, and $X_1X_2X_3X_4$ is not TTTT.

This invention also provides a pharmaceutical composition, which comprises any of the immunostimulatory oligonucleotides defined above, as well as a pharmaceutically acceptable carrier.

The pharmaceutical composition may include an antigen, such as a bacterial antigen, a viral antigen, a fungal antigen or a parasitic antigen. In some instances, the antigen is a vaccine and the composition includes a vaccine adjuvant.

This invention also provides a method of treating a disorder or condition in a subject. The method comprises administering to the subject in need of treatment an effective amount of any of the immunostimulatory oligonucleotides defined above, wherein the disease or condition is an infection, an allergic condition, or cancer.

The method may include treating a subject having or at risk of developing an infection, which is selected from the group consisting of a viral infection, a bacterial infection, a fungal infection, and parasitic infection, or the method may include treating a subject having an allergic condition, such as allergic asthma.

The method may include treating a subject having or at risk of developing one or more of the following types of cancer: basal cell carcinoma; biliary tract cancer; bladder cancer; bone cancer; brain and central nervous system (CNS) cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia; liver cancer; lung cancer; lymphoma including Hodgkin's and Non-Hodgkin's lymphoma; melanoma; myeloma; neuroblastoma; oral cavity cancer; ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, and other carcinomas and sarcomas.

The claimed immunostimulatory oligonucleotides may be administered in conjunction with an anti-cancer therapy, such as cancer medicaments, radiation, surgical procedures, or some combination thereof.

This invention also provides for the use of any of the immunostimulatory oligonucleotides defined above for the preparation of a medicament for the treatment of a disease or condition selected from an infection, an allergic condition, or cancer.

This invention also provides a method for inducing type 1 interferon (IFN) expression or for activating a natural killer (NK) cell. The method includes contacting an NK cell or a cell capable of expressing type 1 IFN with any of the immunostimulatory oligonucleotides defined above in an amount effective to activate the NK cell or to induce expression of type 1 IFN, respectively.

The immunostimulatory oligonucleotides may exist in various forms, including free acid (e.g., zwitterionic) and salt forms (e.g., acid or base addition salt, such as a sodium salt). Therefore, any reference to an immunostimulatory oligonucleotide in the written description and claims encompasses all forms of the oligonucleotide, including its free acid and its salts. The salts include all pharmaceutically acceptable salts.

The invention includes other embodiments and may be practiced or carried out in various ways. The phrasing and terminology used herein is for the purpose of description and should not be regarded as limiting. The use of the words "including," "comprising," "having," "containing," "involving," and variations thereof, is meant to encompass the items listed thereafter and equivalents thereof as well as additional items.

Figure 7:
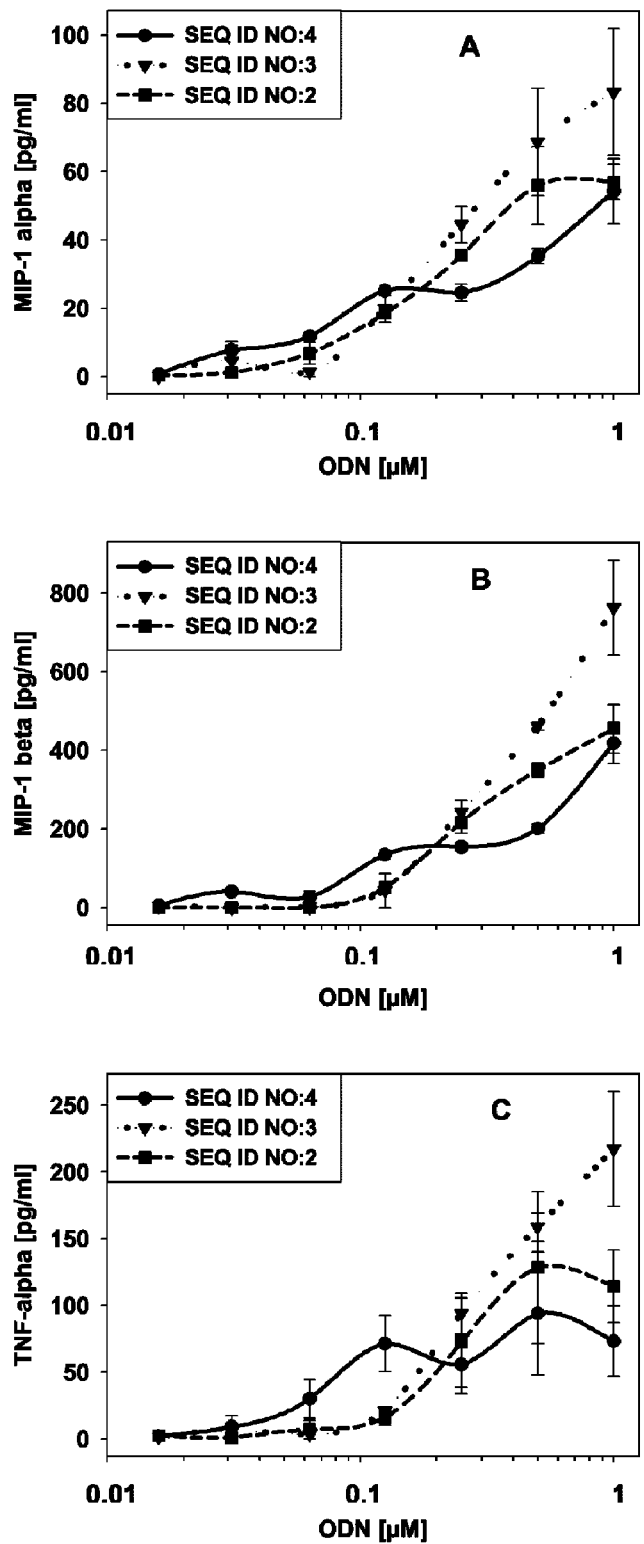
FIG. 7 is a set of graphs depicting cytokine induction in PBMC. PBMC from two donors were incubated with CpG ODN at 0.016-1 μM. After 24 h supernatants were collected and tested by 25-plex (Biosource). Shown is the mean+/–

SEM of cytokines MIP-1α (FIG. 7A), MIP-1β (FIG. 7B), and TNF-α (FIG. 7C) secreted by the PBMC of the two donors.

Figure 8:
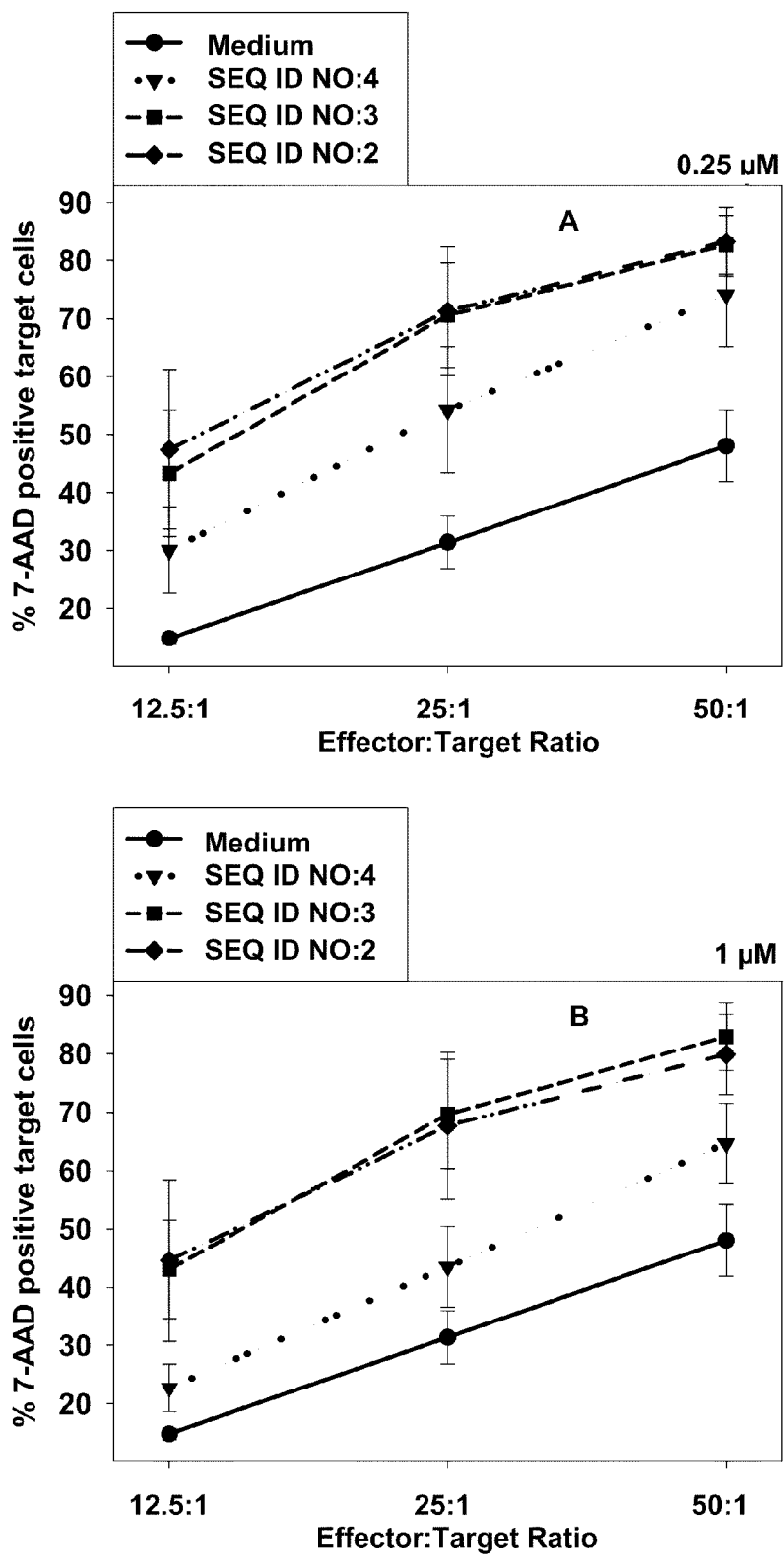

FIG. 8 is a set of graphs depicting human NK cell cytotoxicity. Human PBMC were incubated for 16 h with ODN at 0.25 µM (FIG. 8A) or 1 µM (FIG. 8B) as indicated, followed by incubation with carboxyfluorescein succinimidyl ester (CFSE) labeled target cells (K562, chronic myelogenous leukemia) at different effector:target ratios for an additional 4 h. Cell killing was determined by staining with 7-Amino-actinomycin D (7-AAD) and flow cytometry. Shown is the mean+/− SEM of three donors.

Figure 9:
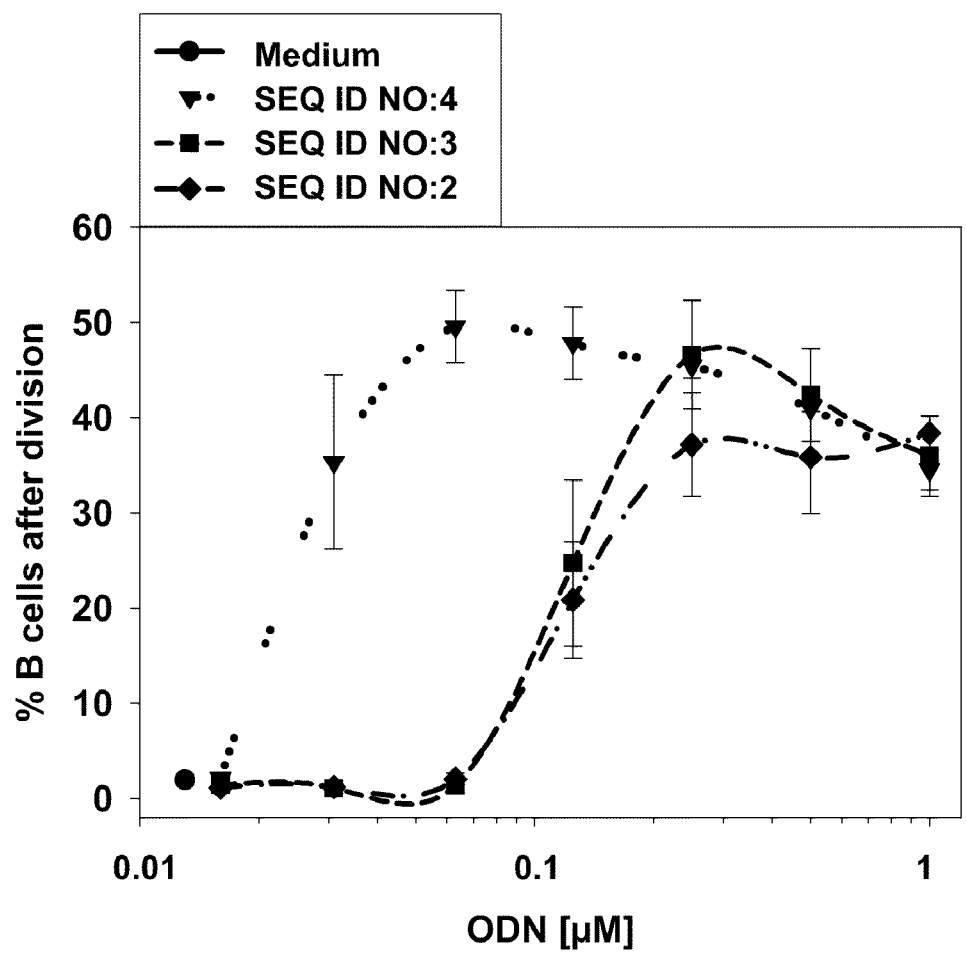

FIG. 9 is a graph depicting human B cell proliferation. CFSE labeled PBMC from three donors were incubated for five days with CpG ODN at 0.016-1 µM, followed by cell surface staining with CD19 to differentiate the B cells. The percentage of B cells with reduced CFSE staining was determined. Shown is the mean+/− SEM of the three donors.

Figure 10:
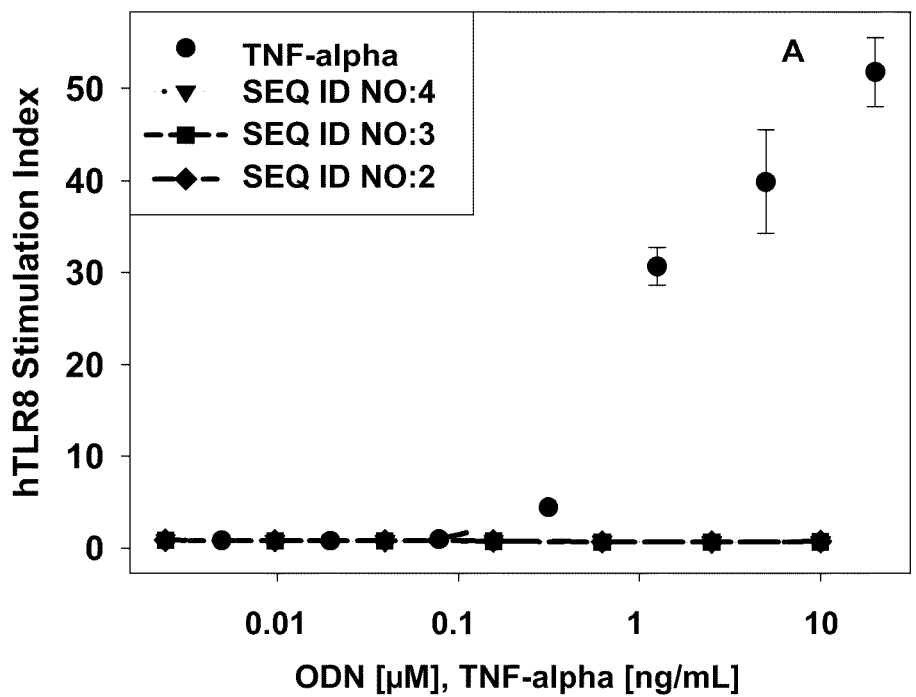
Figure 10:
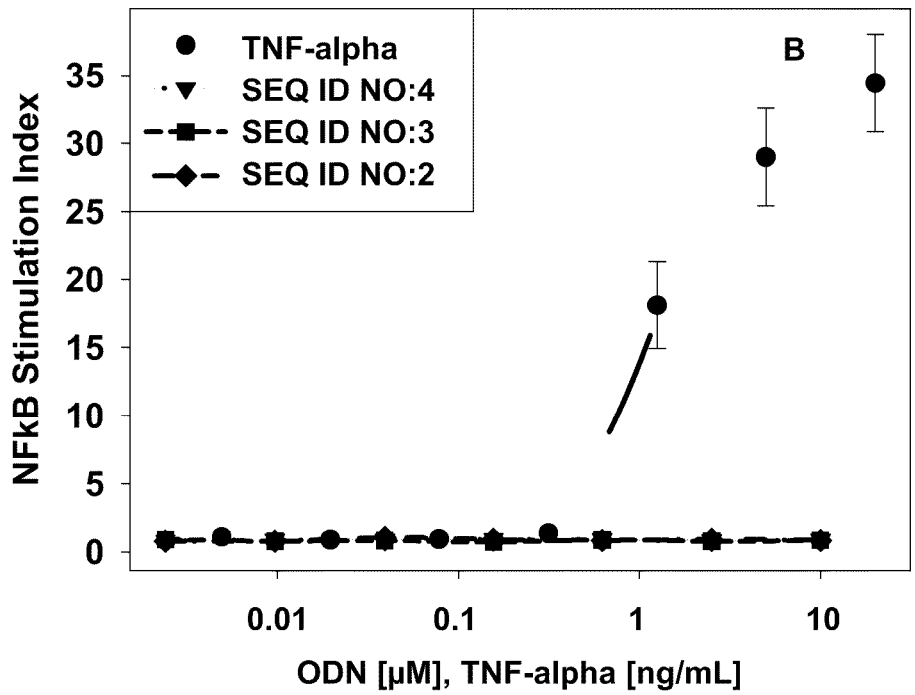

FIG. 10 is a set of graphs depicting human TLR8 and NFκB reporter gene assays. hTLR8-NFκB-293 (FIG. 10A) and NFκB-293 (FIG. 10B) cells were incubated with ODN or TNF-α in concentrations as indicated for 16 h, after which cells were lysed and luciferase activity was determined.

Figure 11:
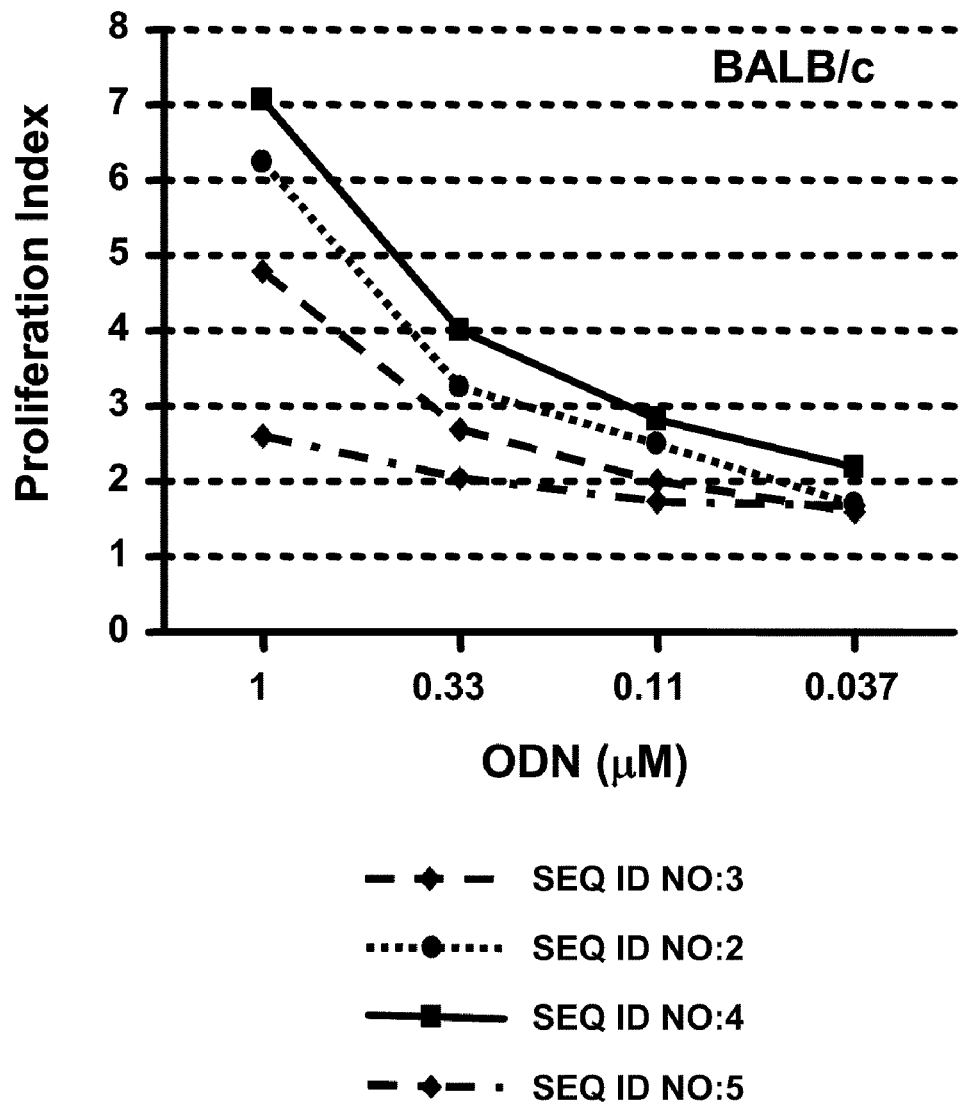

FIG. 11 is a graph depicting mouse B cell proliferation. Naïve BALB/c mouse splenocytes ($4 \times 10^6$/mL) were incubated with media (negative control used as parent population in data analysis) or ODN. Splenocyte (B cell) proliferation measured via CFSE staining following 5-day incubation. Proliferation index measured using the Verity ModFit 5.1 software.

Figure 12:
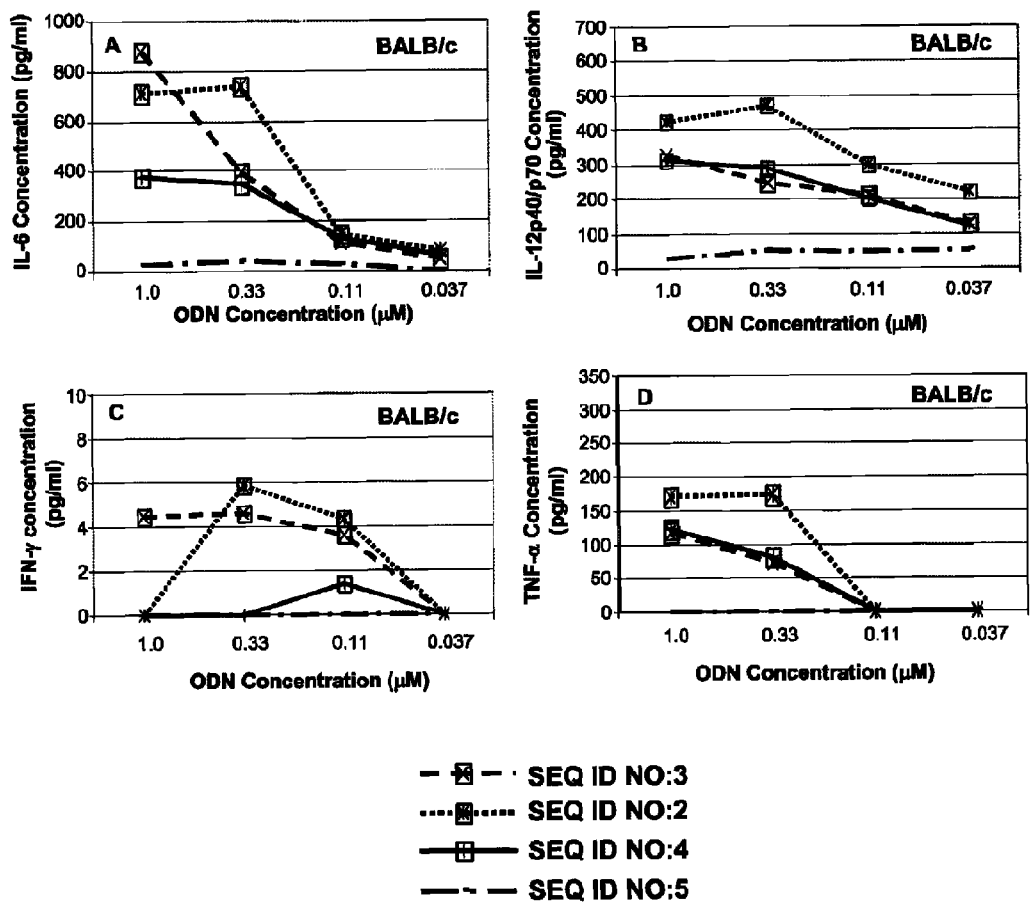

FIG. 12 is a set of graphs depicting in vitro cytokine induction in mouse splenocytes. Naïve BALB/c mouse splenocytes ($5 \times 10^6$/mL) were incubated with ODN. Culture supernatants from 48 h post incubation were tested for IL-6 (FIG. 12A), IL-12 (FIG. 12B), IFN-gamma (FIG. 12C), and TNF-α (FIG. 12D) using Luminex technology (mouse cytokine 20-Plex; Catalogue # LMC 0006, BioSource, Camarillo, Calif.).

Figure 13:
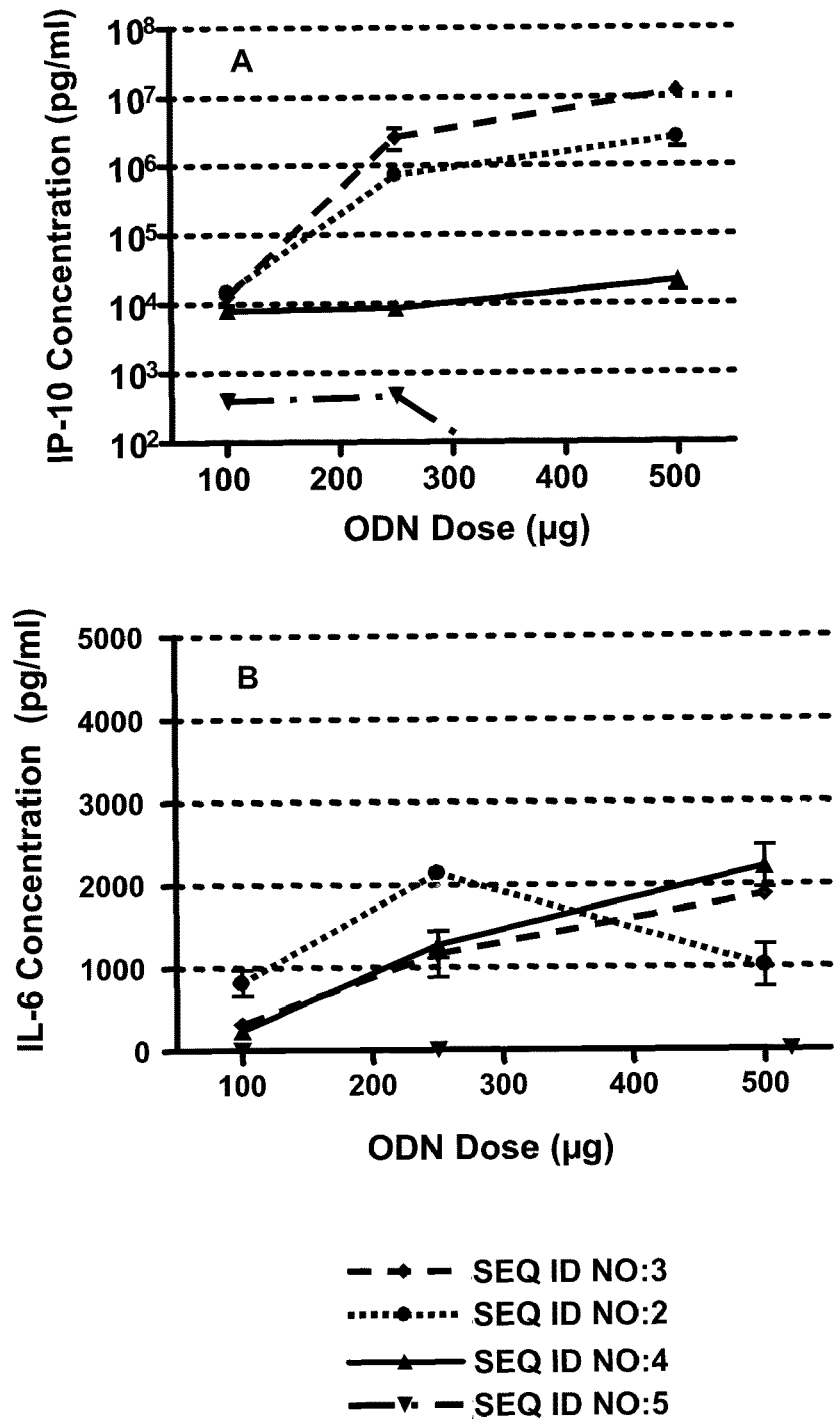

FIG. 13 is a set of graphs depicting in vitro cytokine induction in mouse. Female BALB/c mice (5 per group) were injected subcutaneously (SC) with various doses (100 mg, 250 mg or 500 mg) of CpG ODN or non-CpG control ODN (SEQ ID NO:5). Animals were bled at 3 h post injection and the plasma tested for IP-10 (FIG. 13A) and IL-6 (FIG. 13B) by ELISA.

Figure 14:
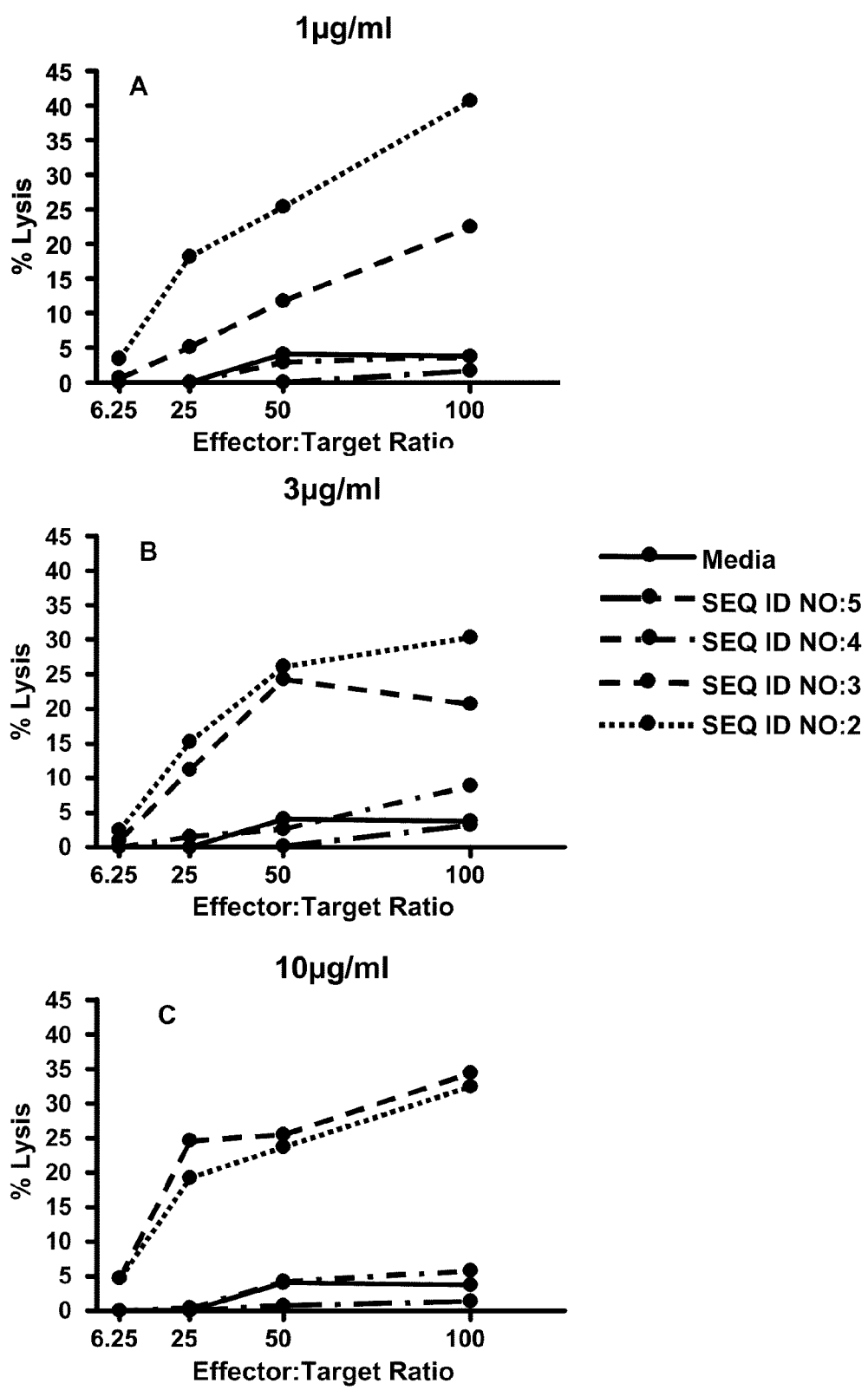

FIG. 14 is a set of graphs depicting augmentation of NK Activity. BALB/c mouse splenocytes ($30 \times 10^6$) were incubated with 0 µg/mL (media alone), 1 µg/mL (FIG. 14A), 3 µg/mL (FIG. 14B) or 10 µg/mL (FIG. 14C) of ODN as indicated for 24 h. NK activity was evaluated using standard 51Cr-release assay with YAC-1 target cells at various effector:target ratios.

Figure 15:
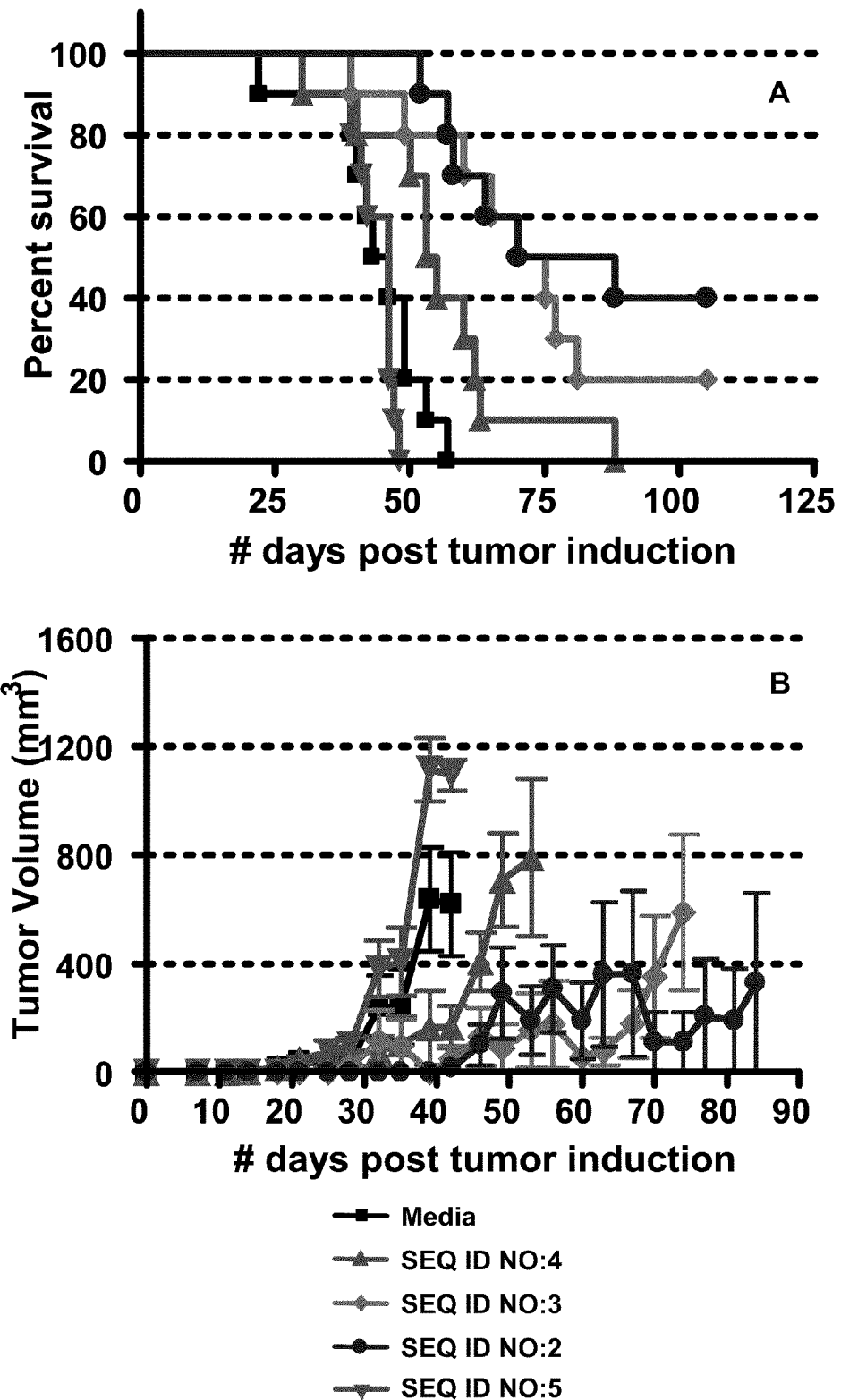

FIG. 15 is a set of graphs depicting Lewis Lung Carcinoma-Survival and Tumor volume. Female C57Bl/6 (~20 g @ start of study; 10 per group) were injected SC with $1 \times 10^5$ LLC cells (ATCC; CRL 1642) in the lower back. ODN (200 mg) was injected SC in the tumor perimeter on day 1 and 3 and then twice weekly. Animals were monitored for tumor growth, as measured by tumor volume (FIG. 15B), and for survival (FIG. 15A). Tumor size (length and width) was measured using a digital vernier caliper. Tumor volume was calculated using the formula: Tumor volume=$(0.4)(ab^2)$, where a is the length (large diameter) and b is the width (smaller diameter). Changes in average tumor volume are indicated until 50% death in each animal group. Mice euthanized on day of tumor measurement are not included on graphs.

Figure 16:
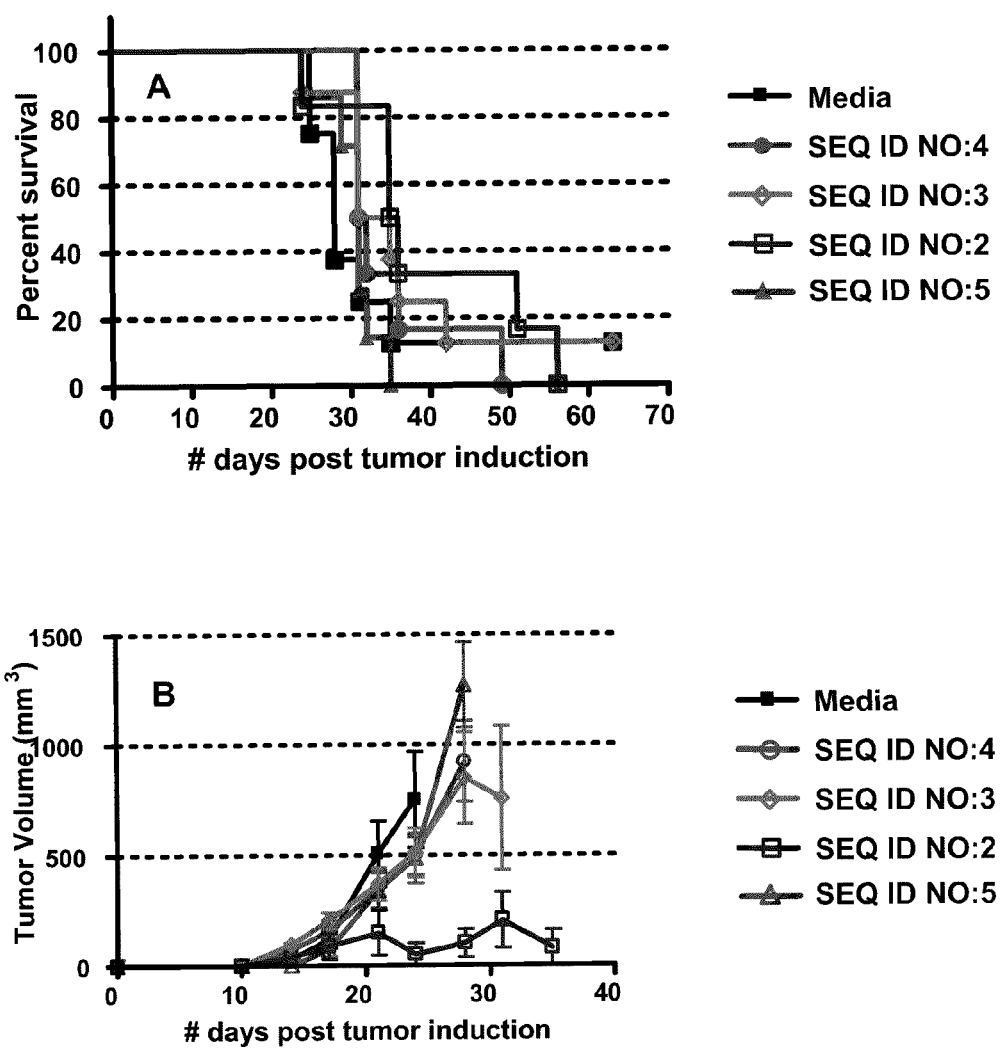

FIG. 16 is a set of graphs depicting Neuroblastoma Therapy. Female A/J mice were injected SC (~20 g @ start of study; 10 per group) with $1 \times 10^6$ neuro-2a cells (ATCC; CCL 131) in the upper left flank. 100 mg ODN was injected SC in the tumor perimeter starting from day 10 post tumor injections. Mice were treated either daily or every 3rd day for 15 days. Animals were monitored for tumor growth, as measured by tumor volume (FIG. 16B), and for survival (FIG. 16A).

DETAILED DESCRIPTION

As discussed above, this invention relates to immunostimulatory nucleic acids and pharmaceutically acceptable salts thereof, including immunostimulatory oligodeoxyribonucleotides. These compounds include a base sequence selected from the following:

```
5' TCGTCGTTTTCGGCGCGCGCCGT 3';                      (SEQ ID NO: 1)

5' T*C_G*T*C*G*T*T*T*T*C*G*G*C*G*C*G*C*G*C*C*G*T 3';  (SEQ ID NO: 2)

5' T*C*G*T*C*G*T*T*T*T*C*G*G*C*G*C*G*C*G*C*C*G*T 3';  (SEQ ID NO: 3)
and

5' TCGTCGTTTTCGGCGCGCGCCGTX₁X₂X₃X₄ 3';              (SEQ ID NO: 6)
``` wherein each of the asterisks "*" in SEQ ID NO: 2 and SEQ ID NO: 3 represents a stabilized internucleotide linkage, the underscore "_" in SEQ ID NO: 2 represents a phosphodiesteror phosphodiester-like internucleotide linkage, $X_1X_2X_3$ and $X_4$ are each independently a nucleotide base, and the sequence $X_1X_2X_3X_4$ is not TTTT. For example, $X_1X_2X_3X_4$ may be TTTA, TTTG, TTTC, TTAA, TTCG, TTCC, TTGG, TTAT, TTCT, TTGT, TATT, TCTT, or TGTT. Unless stated otherwise, any references in the description to an immunostimulatory nucleic acid, oligonucleotide, oligodeoxyribonucleotide, oligoribonucleotide, and so on, refers to the free acid and to any pharmaceutically acceptable salts thereof.

Generally, the 3' and 5' notations in the SEQ ID NOs refer to the relative positions (directionality) of the bases and the corresponding nucleotides in the base sequence, i.e., the notations refer to the 3' and 5' carbon atoms of the five-carbon sugar associated with the labeled base (T and T in SEQ ID NO: 1-3 or $X_4$ and T in SEQ ID NO: 6, respectively) to which another nucleotide may be attached. In some instances, however, the specification states that 3' refers to the 3' end of the nucleic acid, and alternatively or additionally, 5' refers to the 5' end of the nucleic acid. In those instances, the 3' and/or 5' notations indicate that a nucleotide (or nucleoside) is not directly linked to the 3' and/or 5' position, respectively, of the sugar moiety that is associated with the labeled base (nucleotide or nucleoside) in the nucleic acid. Although a nucleotide is not present, the 3' and 5' ends may be attached to a non-nucleotide molecule, such as a linker or an abasic molecule.

As used herein, "nucleic acid" and "oligonucleotide" are used interchangeably and refer to multiple nucleotides, i.e., molecules comprising a sugar moiety (e.g., ribose or deoxyribose) linked to a phosphate group, which may be modified as described below, and to an exchangeable organic base, which is either a substituted pyrimidine—e.g., cytosine (C), thymine (T) or uracil (U)—or a substituted purine—e.g., adenine (A) or guanine (G). As used herein, the terms refer to oligoribonucleotides as well as to oligodeoxyribonucleotides (ODN). The terms may also include polynucleosides, i.e., a polynucleotide minus the phosphate group. Nucleic acid molecules can be obtained from existing nucleic acid sources, e.g., genomic or cDNA, but are preferably synthetic, e.g., produced by nucleic acid synthesis.

As used herein, "immune stimulatory nucleic acid," "immune stimulatory oligonucleotide," "immunostimulatory nucleic acid," and "immunostimulatory oligonucleotide" are equivalent terms and refer to a ribonucleic acid or deoxyribonucleic acid molecule, derivative or analog thereof, characterized by its capacity to induce a functional aspect of a cell of the immune system. Such functional aspect of a cell of the immune system can include, for example, elaboration of a cytokine or chemokine, expression of a cell surface marker, secretion of an antibody, proliferation, or other activity in response to or directed against an antigen or antigen-bearing membrane-bound target.

The immunostimulatory nucleic acids can be synthesized de novo using any number of well known procedures, including, for example, the β-cyanoethyl phosphoramidite method and the nucleoside H-phosphonate method. For a discussion of the β-cyanoethyl phosphoramidite method see Beaucage, S L and Caruthers, M H (1981) *Tetrahedron Lett* 22:1859-62 and Scheme I, below; for a description of the nucleoside H-phosphonate method see Garegg, I L et al. (1986) *Tetrahedron Lett* 27(34):4051-54, Froehler, B C et al. (1986) *Nucl Acid Res* 14(13):5399-407, Garegg, I L et al. (1986) *Tetrahedron Lett* 27(34):4055-58, and Gaffney et al. (1988) *Tetrahedron Lett* 29(22):2619-22). These chemistries can be performed using a variety of commercially available automated nucleic acid synthesizers. These nucleic acids are referred to as synthetic nucleic acids.

Alternatively, the immunostimulatory nucleic acids can be produced on a large scale in plasmids and separated into smaller pieces or administered whole. See e.g., Sambrook, T. et al., Molecular Cloning: A Laboratory Manual, Cold Spring Harbor Laboratory Press, New York (1989). Nucleic acids can be prepared from existing nucleic acid sequences (e.g., genomic or cDNA) using known techniques, such as those employing restriction enzymes, exonucleases or endonucleases. Nucleic acids prepared in this manner are referred to as isolated nucleic acids. An isolated nucleic acid generally refers to a nucleic acid which is separated from components which it is normally associated with in nature. For example, an isolated nucleic acid may be one which is separated from a cell, from a nucleus, from mitochondria or from chromatin. The immunostimulatory nucleic acids described in this specification encompass synthetic and isolated nucleic acids.

For use in vivo, the immunostimulatory nucleic acids may be optionally resistant to degradation (e.g., stabilized). A "stabilized nucleic acid molecule" refers to a nucleic acid that is more resistant to in vivo degradation (e.g., via an exonuclease or endonuclease) than one having the same base sequence and standard phosphate linkages. Nucleic acid stabilization can be accomplished via modifications of the phosphate backbone. Preferred stabilized nucleic acids have a modified phosphate backbone. Generally, modification of the nucleic acid backbone has been shown to provide enhanced immunostimulatory activity of the nucleic acids when administered in vivo. In some instances, immunostimulatory nucleic acids having phosphorothioate linkages possess improved activity and protect the nucleic acid from degradation by intracellular exonucleases and endonucleases. Other nucleic acid backbone modifications include combinations of phosphodiester and phosphorothioate linkages (i.e., chimeric backbones), as well as backbones comprised of alkylphosphonate (e.g., methylphosphonate) groups, alkylphosphorothioate (e.g., methylphosphorothioate) groups, phosphorodithioate groups, ethyl phosphate groups, and the like, including combinations thereof.

Nucleic acids having modified backbones may be prepared using known methods. For example, modified backbones such as phosphorothioates may be synthesized using automated techniques employing either phosphoramidate or H-phosphonate chemistries; aryl- and alkyl-phosphonates can be made as described in U.S. Pat. No. 4,469,863; and alkylphosphotriesters (e.g., ethyl phosphates) can be prepared as described in U.S. Pat. No. 5,023,243 by automated solid phase synthesis using commercially available reagents. Methods for making other nucleic acid backbone modifications and substitutions have been described. See e.g., Uhlmann, E & Peyman, A (1990) *Chem Rev* 90(4):544-84; Goodchild, J (1990) *Bioconjugate Chem* 1(3):165-86.

Nucleic acids which contain a diol, such as tetraethyleneglycol or hexaethyleneglycol, at either or both ends have also been shown to be substantially resistant to nuclease degradation.

Some embodiments of the immunostimulatory nucleic acids may have partially stabilized, chimeric backbones, which comprise soft or semi-soft backbones. As noted earlier, a chimeric backbone includes phosphodiester and modified backbone linkages. A soft oligonucleotide is an immunostimulatory nucleic acid having a partially stabilized backbone, in which phosphodiester or phosphodiester-like internucleotide linkages occur only within and immediately adjacent to at least one internal pyrimidine-guanine (YG) dinucleotide base sequence. The internal YG dinucleotide thus includes phosphodiester or phosphodiester-like internucleotide linkages that (i) connect the pyrimidine nucleoside and the guanosine or deoxyguanosine moieties (i.e., Y_G) and (ii) connect an adjacent nucleotide or nucleotides 5', 3', or both 5' and 3' to the internal YG dinucleotide. Preferably, the adjacent phosphodiester or phosphodiester-like internucleotide linkage is an internal internucleotide linkage.

A semi-soft oligonucleotide is an immunostimulatory nucleic acid having a partially stabilized backbone, in which phosphodiester or phosphodiester-like internucleotide linkages occur only within at least one internal pyrimidine-guanine (YG) dinucleotide base sequence. Semi-soft oligonucleotides can have a number of advantages over immunostimulatory oligonucleotides with fully stabilized backbones. For instance, semi-soft oligonucleotides may possess increased immunostimulatory potency relative to corresponding fully stabilized immunostimulatory oligonucleotides.

A phosphodiester-like internucleotide linkage is a phosphorus-containing bridging group that is chemically and/or diastereomerically similar to a phosphodiester bond. Measures of similarity to phosphodiester bonds include susceptibility to nuclease digestion and the ability to activate RNAse H. Thus, for example, phosphodiester oligonucleotides, but not phosphorothioate oligonucleotides, are susceptible to nuclease digestion, while both phosphodiester and phosphorothioate oligonucleotides activate RNAse H. In a preferred embodiment the phosphodiester-like internucleotide linkage is a boranophosphate (or equivalently, boranophosphonate) linkage. See e.g., U.S. Pat. No. 5,177,198, U.S. Pat. No. 5,859,231, U.S. Pat. No. 6,160,109, U.S. Pat. No. 6,207,819, and Sergueev, D S & Shaw, B S (1998) *J Am Chem Soc* 120:9417-27. In another preferred embodiment, the phosphodiester-like internucleotide linkage is diasteromerically pure Rp phosphorothioate. In some embodiments, the term "phosphodiester-like internucleotide linkage" specifically excludes phosphorodithioate and methylphosphonate internucleotide linkages.

Scheme I shows one process for preparing oligodeoxyribonucleotides using solid phase β-cyanoethyl phosphoramidite methodology. The process employs monomeric β-cyanoethyl-diisopropylphosphoramidite building blocks, T-Amidite, G Amidite, and C Amidite, whose structures are shown, below:

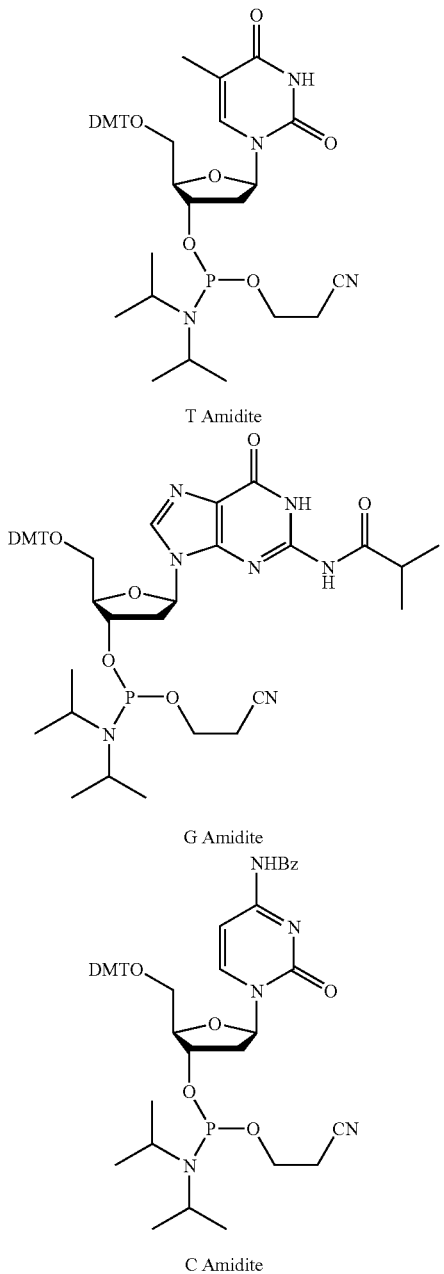

T Amidite

G Amidite

C Amidite

The monomeric building blocks contain an acid labile 4,4'-dimethoxytrityl (DMT) group, which protects the 5'-hydroxy function of each deoxyribose moiety. The building blocks also contain a β-cyanoethyl group, which protects the phosphite (or phosphate) group during synthesis, and base-labile acyl groups (e.g., isobutanoyl and benzoyl), which protect the primary amino functions of the nucleobases (guanine and cytosine).

Scheme I illustrates the preparation of an ODN (formula XII) which contains n bases ($B_1$, $B_2$, $B_3$, ... $B_n$) and nucleosides. The synthesis is performed using a computer-controlled solid phase oligonucleotide synthesizer, which includes a flow-through reactor module comprised of a stainless steel column containing a packed bed of solid support media (e.g., controlled pore glass, polystyrene, etc.). The synthesizer delivers reagents and wash-solutions and monitors the course of the process. No intermediates are isolated during the chain-lengthening portion of the process. The starting material is a first nucleoside (formula I) which includes a DMT-protected 5'-hydroxy function and a nucleobase $B_1$. The first nucleoside is connected to the solid support media at the 3'-position of the deoxyribose moiety via a succinyl linker. As noted above, the nucleobases having primary amine groups include base-labile acyl groups to prevent undesirable side reactions during processing.

The process includes n-1 cycles, each comprised of four primary steps—(a) deblocking or detritylation of the 5'-end of the solid-supported ODN; (b) coupling of the requisite monomeric building block (T-Amidite, G-Amitide or C-Amidite) to the deprotected 5'-end of the ODN; (c) oxidation (e.g., thiolation) of the phosphite bridge, which links the nucleoside installed in the coupling step to the solid-supported ODN; and (d) capping of any unreacted deprotected starting material or deprotected intermediates. An acetonitrile (ACN) wash between each primary step (a-d) removes excess reactants (e.g., monomeric building blocks). During the process, the ODN is assembled in the 3' to 5' direction. Following the n-1 cycles, the full-length ODN (having a DMT group at the 5'-end) is cleaved from the solid support, the primary amines of the nucleobases are deprotected, the ODN is purified by column chromatography, and the DMT group is removed to furnish the desired ODN (XII) or its salt.

As noted above, and as shown in Scheme I, the first step ($a_1$) in the ODN synthesis includes removal of the DMT protective group from the 5'-hydroxy function of the starting material (formula I) via brief contact with an acid, e.g., dichloroacetic acid (DCA) in toluene. Following deprotection, the 5'-hydroxy group (formula II) is available for reaction in the coupling step ($b_1$) with the requisite phosphoramidite building block (formula III). The phosphoramidite monomer (formula III) is first activated with a coupling agent, such as saccharin N-methylimidazole salt (SMI), and is then reacted with the deprotected starting material (formula II) to give a two-base intermediate (formula IV). Next, the phosphite moiety, which links the newly installed $B_2$-nucleoside to the $B_1$-nucleoside, is oxidized ($c_1$) to a more stable pentavalent phosphotriester bridge. If a phosphorothioate linkage (X=S in formula V) is desired, the intermediate (formula IV) is reacted with a sulfur-transferring reagent, e.g., a thiolation reagent such as 5-amino-3H-1,2,4-dithiazole-3-thione (xanthane hydride) in pyridine; if a phosphodiester linkage (X=O in formula V) is desired, the intermediate (formula IV) is reacted with iodine/water. In the final step ($d_1$) of the first cycle, any unreacted 5'-hydroxy groups (formula II) are capped by reaction with an acylating agent, e.g., a mixture of isobutanoic acid anhydride and N-methylimidazole in ACN and pyridine. This prevents incomplete ODN strands from reacting later in the ODN assembly process.

Scheme I
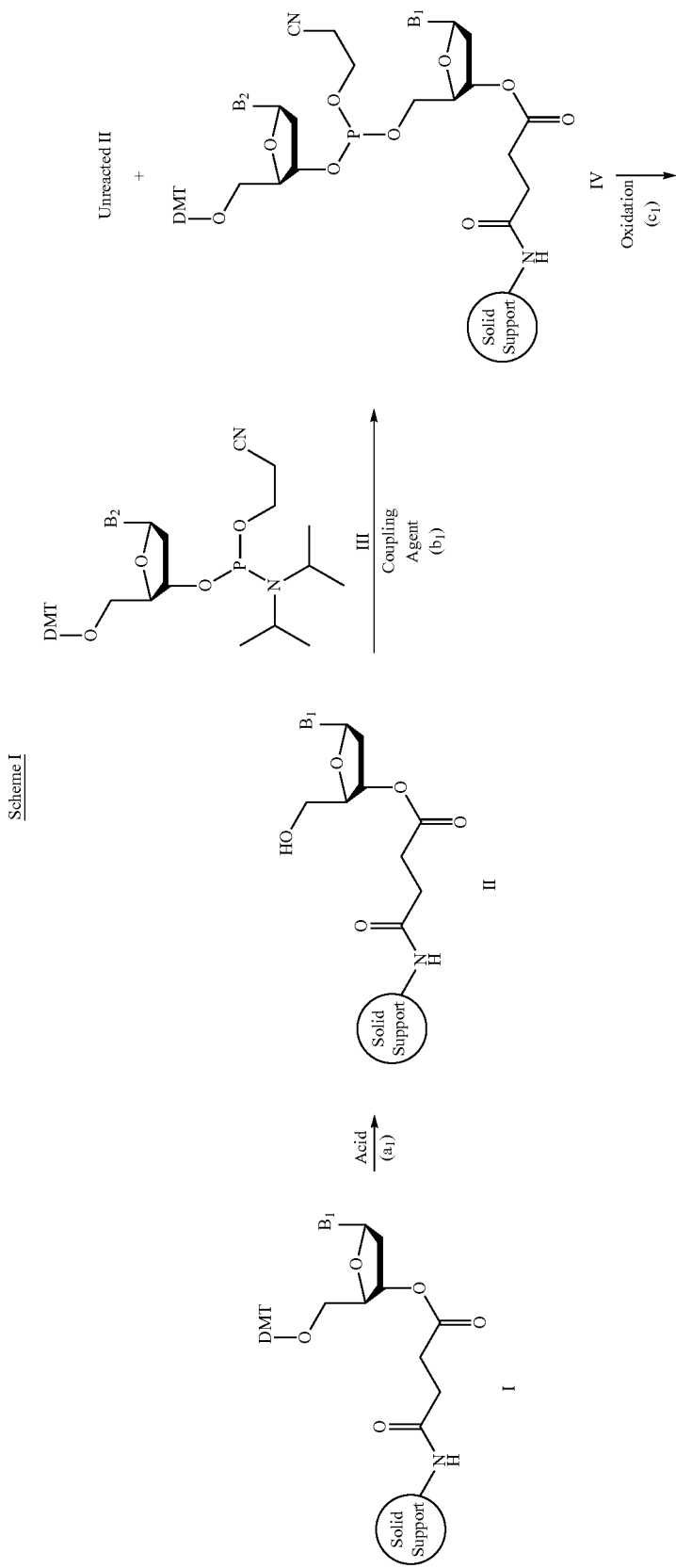

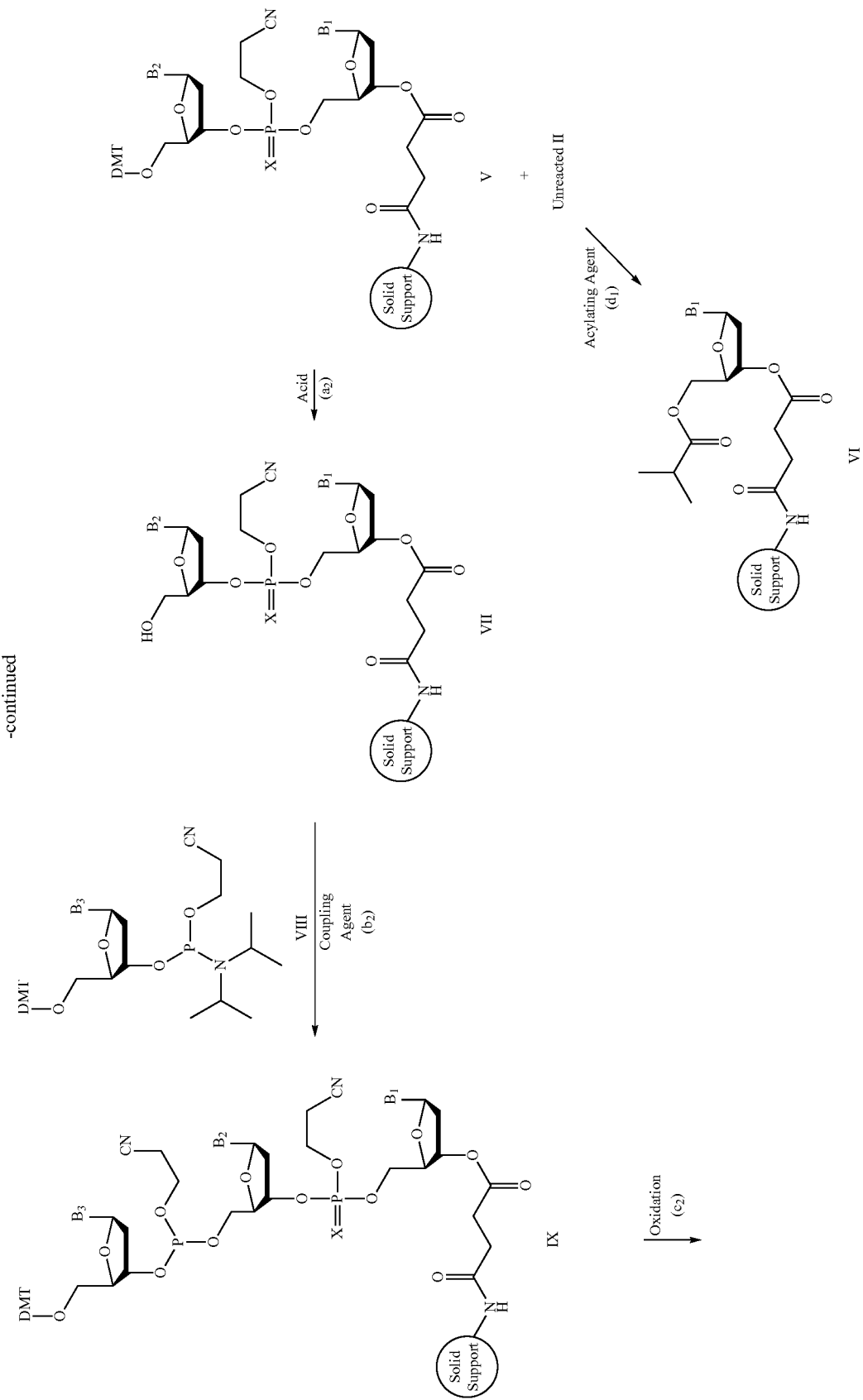

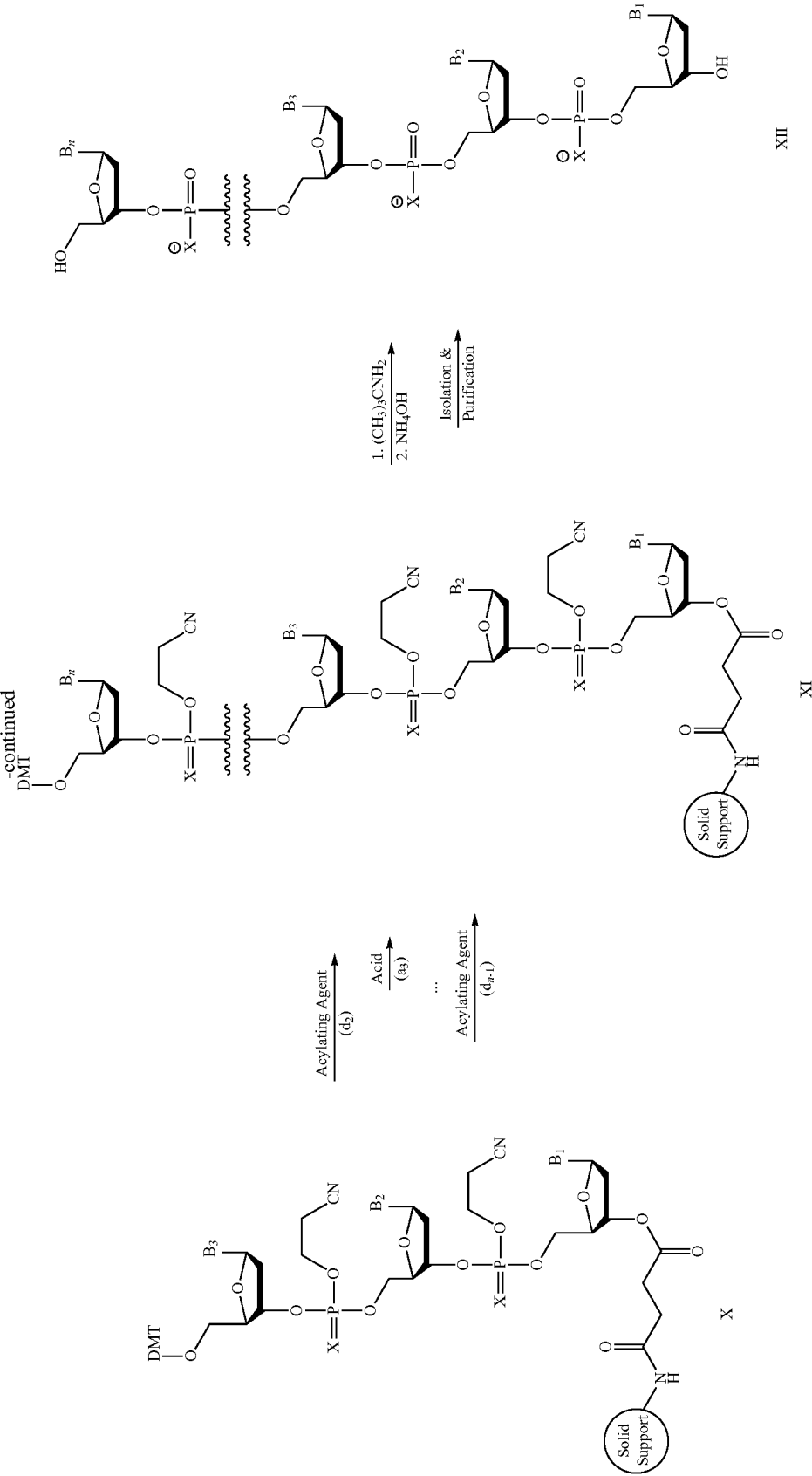

Subsequent cycles begin with the removal of the DMT group from the 5'-hydroxy function of the newly added nucleoside. Thus, as shown in Scheme I, the protected dinucleotide (formula V) is contacted ($a_2$) with acid to reveal the 5'-hydroxy moiety (formula VII) which is subsequently reacted ($b_2$) with the requisite phosphoramidite building block (formula VIII) following monomer activation. Oxidation ($c_2$) of the newly-formed phosphite moiety (formula IX), linking the newly installed $B_3$-nucleoside to the $B_2$-nucleoside, gives a trinucleotide (formula X) having a DMT-protected 5'-hydroxy end. Capping ($d_2$) of any unreacted 5'-hydroxy groups (formula VII) via reaction with an acylating agent completes the second cycle. Note that substituent X in formula VII and in formula IX-XII is S or O, depending on whether a phosphorothioate or a phosphodiester internucleotide linkage is desired.

After the last (n-1) cycle is completed, the β-cyanoethyl protective groups are removed by contacting the ODN (formula XI) with a hindered primary aliphatic amine, e.g., tert-butylamine. The resulting DMT-capped ODN (not shown) is subsequently contacted with a base, e.g., concentrated ammonium hydroxide, which cleaves the base-labile succinyl linker, liberating the DMT-protected ODN from the solid support. Contact with the base also deprotects the primary amines on the nucleobases.

The finished ODN (formula XII) is isolated and purified by ion exchange column chromatography. The method exploits the higher affinity of the DMT-capped full-length ODN in the stationary phase relative to the incomplete ODN (e.g., formula VI) which lack a terminal 5'-DMT group. To obtain a sodium salt of the ODN, the crude aqueous ammonia hydroxide wash solution, which contains the DMT-capped ODN, is adsorbed onto the ion exchange column and washed with aqueous NaOH. The incomplete ODN are removed from the column by washing with an aqueous NaCl/NaOH. This leaves the DMT-capped ODN bound to the stationary phase. The DMT-group is subsequently removed by washing with aqueous acetic acid, followed by water, and by aqueous NaOH to reconvert the ODN (formula XII) back to the sodium salt. The ODN is then purified on the column using a linear gradient of NaCl in NaOH. Fractions are collected, and mock pools are prepared and analyzed by HPLC and capillary gel electrophoresis (CGE). Fractions of the corresponding mock pool which meet the ODN specifications are pooled together, concentrated and desalted using tangential flow filtration (TFF). The resulting retentate is filtered (e.g., using a 0.22 μm filter) and the solution is lyophilized to give the finished ODN.

The immunostimulatory nucleic acids may be used to treat a subject to induce an immune response or to treat an immune related disease such as, for example, infectious disease, cancer, and allergic disorders.

As used herein, "subject" refers to a human being and to vertebrate animals, including, but not limited to a dog, cat, horse, cow, pig, sheep, goat, chicken, monkey, rabbit, rat, mouse, etc.

As used herein, the terms "treat," "treating," "treated," and variations thereof, refer to reversing, alleviating, inhibiting the progress of, or preventing a disease, disorder or condition to which such term applies, or to reversing, alleviating, inhibiting the progress of, or preventing one or more symptoms of such disease, disorder or condition. "Treatment" refers to the act of "treating."

Thus, treating refers to prophylactic treatment—i.e., treatment that increases the resistance of a subject to developing a disease, or decreases the likelihood that the subject will develop a disease, or slows the development of the disease—and refers to treatment after the subject has developed the disease—i.e., treatment that seeks to reduce or eliminate the disease or to prevent the disease from becoming worse. For example, when used with respect to the treatment of an infectious disease, treating refers to prophylactic treatment, which increases the resistance of a subject to a microorganism, or decreases the likelihood that the subject will develop an infectious disease to the microorganism, as well as to a treatment after the subject has been infected in order to fight the infectious disease, e.g., reduce or eliminate it altogether or prevent it from becoming worse. When used with respect to a disease such as cancer the terms refer to (i) preventing or (ii) delaying the development of a cancer, (iii) reducing the symptoms of cancer, (iv) inhibiting or (v) slowing the growth of an established cancer or a combination of (i)-(v).

Thus, the nucleic acids are useful as prophylactics for inducing immunity in a subject at risk of developing an infection from an infectious organism or at risk of developing an allergic disorder or at risk of developing cancer. A "subject at risk" is generally any subject, as defined earlier, who exhibits one or more risk factors associated with a disease, condition or disorder. A risk factor is anything that may increase the chance of developing the disease, condition or disorder. For example, risk factors for infectious or allergy-related diseases include travel to an area where a particular type of infectious agent or allergen is found; contact with bodily fluids, through lifestyle, occupation, medical procedures, etc., which may contain infectious organisms; residence in an area where an infectious organism or an allergen has been identified and where direct exposure to an infectious agent or allergen has occurred; residence in an area subject to terrorist attack (e.g., bio-warfare). Subjects at risk of developing an infection also include general populations to which a medical agency recommends vaccination with a particular infectious organism antigen. If the antigen is an allergen and the subject develops allergic responses to that particular antigen and the subject is exposed to the antigen, i.e., during pollen season, then that subject is at risk of exposure to the antigen.

Risk factors for developing cancer include genetic predisposition and family history of certain cancers; prior treatment for cancer; growing older (e.g., age 65 or older); use of tobacco products; poor diet (e.g., high fat diet); obesity; excessive consumption of alcohol (e.g., more than 2 ounces/day); lack of exercise; exposure to ionizing radiation (e.g., radioactive fallout, x-rays, radon); exposure to excessive sunlight and to cancer-causing chemicals, including asbestos, benzene, benzidine, cadmium, nickel, or vinyl chloride; infection with some viruses and bacteria, including human papilloma viruses (HPVs), hepatitis B and hepatitis C viruses, human T-cell leukemia/lymphoma virus (HTLV-1), human immunodeficiency virus (HIV), Epstein-Barr virus (EBV), human herpes virus 8 (HHV8), and *Helicobacter pylori* bacterium; and treatment with certain hormones, including estrogen, either alone or in combination with progestin, and diethylstilbestrol (DES).

The nucleic acids are also useful as therapeutics in the treatment of infectious disease, cancer and allergic disorders.

A "subject having an infection" is a subject that has been exposed to an infectious pathogen and has acute or chronic detectable levels of the pathogen in the body. The nucleic acids can be used alone, or in conjunction with other therapeutic agents such as an antigen or an antimicrobial medicament to mount an immune response that is capable of reducing the level of, or eradicating, the infectious pathogen. The method entails administering to a subject having or at risk of developing an infection an effective amount of an immunostimulatory nucleic acid of the invention to treat the infection.

The method can be used to treat viral, bacterial, fungal, and parasitic infections in human and non-human vertebrate subjects.

As used herein, "infection," and equivalently, "infectious disease," refer to a disease arising from the presence of a foreign microorganism in the body of a subject. A foreign microorganism may be a virus, a bacterium, a fungus, or a parasite. Examples of infectious viruses include: Retroviridae (e.g., human immunodeficiency viruses, such as HIV-1 (also referred to as HTLV-III, LAV or HTLV-III/LAV, or HIV-III); and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); *Arena viridae* (hemorrhagic fever viruses); Reoviridae (e.g., reoviruses, orbiviurses and rotaviruses); Birnaviridae: Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses); Poxyiridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria include: *Actinomyces israelii, Bacillus anthracis Bacteroides* spp., *Borrelia burgdorferi, Chlamydia trachomatis, Clostridium perfingens Clostridium tetani, Corynebacterium diphtheriae, Corynebacterium* spp., *Enterobacter aerogenes, Enterococcus* sp., *Erysipelothrix rhusiopathiae, Fusobacterium nucleatum, Haemophilus influenzae, Helicobacter pyloris, Klebsiella pneumoniae, Legionella pneumophilia, Leptospira, Listeria monocytogenes, Mycobacteria* spp. (e.g., *M. tuberculosis M. avium, M. intracellulare, M. kansasii, M. gordonae*), *Neisseria gonorrhoeae, Neisseria meningitidis, Pasturella multocida*, pathogenic *Campylobacter* sp., *Staphylococcus aureus, Streptobacillus moniliformis, Streptococcus* (anaerobic spp.), *Streptococcus* (viridans group), *Streptococcus agalactiae* (Group B *Streptococcus*), *Streptococcus boris, Streptococcus faecalis, Streptococcus pneumoniae, Streptococcus pyogenes* (Group A *Streptococcus*), *Treponema pallidium*, and *Treponema pertenue*.

Examples of infectious fungi include: *Candida albicans, Cryptococcus neoformans, Histoplasma capsulatum, Coccidioides immitis*, and *Blastomyces derifiatitidis.*

Other infectious organisms (i.e., protists) include *Plasmodium* spp., such as *Plasmodium falciparum, Plasmodium malariae, Plasmodium ovale*, and *Plasmodium vivax*. Bloodborne and/or tissue parasites include *Plasmodium* spp., *Babesia microti, Babesia divergens, Leishmania tropica, Leishmania* spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*.

The foregoing lists of viruses, bacteria, fungi, and other infectious microorganisms are understood to be representative and not limiting. Other medically relevant microorganisms have been described extensively in the literature, e.g., see C. G. A Thomas, *Medica Microbiology*, Bailliere Tindall, Great Britain (1983), the entire contents of which is hereby incorporated by reference.

Although many of the microbial agents described above relate to human disorders, the invention is also useful for treating non-human vertebrates. Non-human vertebrates are also capable of developing infections which can be prevented or treated with the immunostimulatory nucleic acids disclosed herein. For instance, in addition to the treatment of infectious human diseases, the methods of the invention are useful for treating infections of animals.

Infectious viruses of both human and non-human vertebrates include retroviruses, RNA viruses and DNA viruses. This group of retroviruses includes both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and myeloblastosis virus (AMV)) and C-type group B (including feline leukemia virus (FeLV), gibbon ape leukemia virus (GALV), spleen necrosis virus (SNV), reticuloendotheliosis virus (Rv) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV). The foamy viruses include human foanay virus (HFV), simian foamy virus (SFV) and bovine foamy virus (BFV).

Examples of other RNA viruses that are infectious agents in vertebrate animals include, but are not limited to members of the family Reoviridae, including the genus Orthoreovirus (multiple serotypes of both mammalian and avian retroviruses), the genus Orbivirus (Bluetongue virus, Eugenangee virus, Kemerovo virus, African horse sickness virus, and Colorado Tick Fever virus), the genus Rotavirus (human rotavirus, Nebraska calf diarrhea virus, simian rotavirus, bovine or ovine rotavirus, avian rotavirus); the family Picornaviridae, including the genus Enterovirus (poliovirus, Coxsackie virus A and B, enteric cytopathic human orphan (ECHO) viruses, hepatitis A virus, Simian enteroviruses, Murine encephalomyelitis (ME) viruses, Poliovirus muris, Bovine enteroviruses, Porcine enteroviruses, the genus Cardiovirus (Encephalomyocarditis virus (EMC), Mengovirus), genus Rhinovirus (Human rhinoviruses including at least 113 subtypes; other rhinoviruses), the genus Apthovirus (Foot and Mouth disease virus (FMDV); the family Calciviridae, including Vesicular exanthema of swine virus, San Miguel sea lion virus, Feline picornavirus and Norwalk virus; the family Togaviridae, including the genus Alphavirus (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus Flavivirus (Mosquito-borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type (possible separate genus); the family paramyxoviridae, including the genus Paramyxoviru (Parainfluenza virus type 1, Sendai virus, Hemadsorption virus, Parainfluenza viruses types to Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus Pneumonia virus); the family Rhabdoviridae, including the genus Vesiculovirus (VSV), (Chandipura virus, Flanders-Hart Park virus), the genus Lyssavirus (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), Hepatitis virus, Human enteric corona virus, and Feline infectious peritonitis (Feline coronavirus).

Illustrative DNA viruses that are infectious agents in vertebrate animals include, but are not limited to, the family Poxyiridae, including the genus Orthopoxvirus (Variola major, Variola minor, Monkey pox Vaccinia, Cowpox, Buffalopox, Rabbitpox, Ectromelia), the genus Leporipoxvirus (Myxoma, Fibroma), the genus Avipoxvirus (Fowlpox, other avian poxvirus), the genus Capripoxvirus (sheep-pox, goatpox), the genus Suipoxvirus (Swinepox), the genus Parapoxvirus (contagious pustular dermatitis virus, pseudocowpox, bovine popular stomatitis virus); the family Iridoviridae (African swine fever virus, Frog viruses 2 and 3, Lymphoystis virus offish); the family Herpesviridae, including the alpha-Herpesviruses (Herpes Simplex Types 1 and 2, VariceUa-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus), the Beta-herpesviruses (Human cytomegalovirus and cytomegaloviruses of swine and monkeys); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus Mastadenovirus (Human subgroups A, B, C, D, and ungrouped); simian adenoviruses (at least 23 serotypes), infectious canine hepatitis, and adenoviruses of cattle, pigs, sheep, frogs and many other species, the genus Aviadenovirus (Avian adenoviruses); and non-cultivatable adenoviruses, the family Papoviridae, including the genus Papillomavirus (Human papilloma viruses, bovine papilloma viruses, Shope rabbit papilloma virus, and various pathogenic papilloma viruses of other species), the genus Polyomavirus (polyomavirus, Simian vacuolating agent (SV-40), Rabbit vacuolating agent (RKV), K virus, BK virus, JC virus, and other primate polyoma viruses such Lymphotrophic papilloma virus); the family Parvoviridae including the genus Adeno-associated viruses, the genus Parvovirus (Feline panleukopenia virus, bovine parvovirus, canine parvovirus, Aleutian mink disease virus, etc.). Finally, DNA viruses may include viruses which do not fit into the above families, such as Kuru and Creutzfeldt-Jacob disease viruses and chronic infectious neuropathic agents (CHINA virus).

The nucleic acids may be administered to a subject with an anti-microbial agent. An "anti-microbial agent," as used herein, refers to a naturally-occurring, synthetic, or semisynthetic compound, which is capable of killing or inhibiting infectious microorganisms. The type of anti-microbial agent depends on the type of microorganism with which the subject is infected or at risk of becoming infected. Antimicrobial agents include, but are not limited to, anti-bacterial agents, anti-viral agents, antifungal agents and anti-parasitic agents. Phrases such as "anti-infective agent," "anti-bacterial agent," "anti-viral agent," "anti-fungal agent," "anti-parasitic agent," and "parasiticide" have well-established meanings to those of ordinary skill in the art and are defined in standard medical texts. Briefly, anti-bacterial agents kill or inhibit bacteria, and include antibiotics as well as other synthetic or natural compounds having similar functions. Antibiotics are low molecular weight molecules which are produced as secondary metabolites by cells, such as microorganisms. In general, antibiotics interfere with one or more bacterial functions or structures which are specific for the microorganism and which are not present in host cells. Anti-viral agents can be isolated from natural sources or synthesized and are useful for killing or inhibiting viruses. Anti-fungal agents are used to treat superficial fungal infections as well as opportunistic and primary systemic fungal infections. Anti-parasite agents kill or inhibit parasites.

Antibacterial agents kill bacteria or inhibit the growth or function of bacteria. A large class of antibacterial agents is antibiotics. Antibiotics, which are effective for killing or inhibiting a wide range of bacteria, are referred to as broad spectrum antibiotics. Other types of antibiotics are predominantly effective against the bacteria of the class gram-positive or gram-negative. These types of antibiotics are referred to as narrow spectrum antibiotics. Other antibiotics which are effective against a single organism or disease and not against other types of bacteria, are referred to as limited spectrum antibiotics. Antibacterial agents are sometimes classified based on their primary mode of action. In general, antibacterial agents are cell wall synthesis inhibitors, cell membrane inhibitors, protein synthesis inhibitors, nucleic acid synthesis or functional inhibitors, and competitive inhibitors.

Antiviral agents are compounds which prevent infection of cells by viruses or replication of the virus within the cell. There are many fewer antiviral drugs than antibacterial drugs because the process of viral replication is so closely related to DNA replication within the host cell, that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g., amantadine), synthesis translation of viral mRNA (e.g., interferon), replication of viral RNA or DNA (e.g., nucleoside analogues), maturation of new virus proteins (e.g., protease inhibitors), budding and release of the virus.

Nucleotide analogues are synthetic compounds that are similar to nucleotides, but have an incomplete or abnormal deoxyribose or ribose group. Once the nucleotide analogues are in the cell, they are phosphorylated, producing the triphosphate form which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varieella-zoster virus), gancyclovir (useful for the treatment cytomegalovirus), idoxuridine, ribavirin (useful for the treatment of respiratory syncytial virus), dideoxyinosine, dideoxycytidine, and zidovudine (azidothymidine).

Anti-fungal agents are useful for the treatment and prevention of infective fungi. Anti-fungal agents are sometimes classified by their mechanism of action. Some anti-fungal agents function as cell wall inhibitors by inhibiting glucose synthase. These include, but are not limited to, basiungin/ECB. Other anti-fungal agents function by destabilizing membrane integrity. These include, but are not limited to, immidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, and terbinafine. Other anti-fungal agents function by breaking down chitin (e.g., chitinase) immunosuppression (501 cream).

The immunostimulatory nucleic acids may be used, either alone or in combination with an anti-cancer therapy, for the treatment of cancer. The method entails administering to a subject having or at risk of developing cancer an effective amount of an immunostimulatory nucleic acid of the invention to treat cancer.

A "subject having cancer" is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g., small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In one embodiment the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma.

Cancer is one of the leading causes of death in companion animals (i.e., cats and dogs). Malignant disorders commonly diagnosed in dogs and cats include, but are not limited to, lymphosarcoma, osteosarcoma, mammary tumors, mastocytoma, brain tumor, melanoma, adenosquamous carcinoma, carcinoid lung tumor, bronchial gland tumor, bronchiolar adenocarcinoma, fibroma, myxochondroma, pulmonary sarcoma, neurosarcoma, osteoma, papilloma, retinoblastoma, Ewing's sarcoma, Wilms' tumor, Burkitt's lymphoma, microglioma, neuroblastoma, osteoclastoma, oral neoplasia, fibrosarcoma, osteosarcoma and rhabdomyosarcoma. Other neoplasms in dogs include genital squamous cell carcinoma, transmissible venereal tumor, testicular tumor, seminoma, Sertoli cell tumor, hemangiopericytoma, histiocytoma, chloroma (granulocytic sarcoma), corneal papilloma, corneal squamous cell carcinoma, hemangiosarcoma, pleural mesothelioma, basal cell tumor, thymoma, stomach tumor, adrenal gland carcinoma, oral papilomatosis, hemangioendothelioma and cystadenoma. Additional malignancies diagnosed in cats include follicular lymphoma, intestinal lymphosarcoma, fibrosarcoma and pulmonary squamous cell carcinoma. The ferret, an ever-more popular house pet, is known to develop insulinoma, lymphoma, sarcoma, neuroma, pancreatic islet cell tumor, gastric MALT lymphoma and gastric adenocarcinoma.

The immunostimulatory nucleic acids described herein may also be administered in conjunction with an anti-cancer therapy. Anti-cancer therapies include cancer medicaments, radiation and surgical procedures. As used herein, a "cancer medicament" refers to an agent which is administered to a subject for the purpose of treating a cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

The use of immunostimulatory nucleic acids in conjunction with immunotherapeutic agents such as monoclonal antibodies is able to increase long-term survival through a number of mechanisms including significant enhancement of antibody-dependent cellular cytotoxicity (ADCC), activation of NK cells and an increase in IFN-$\alpha$ levels. ADCC can be performed using an immunostimulatory nucleic acid in combination with an antibody specific for a cellular target, such as a cancer cell. When the immunostimulatory nucleic acid is administered to a subject in conjunction with the antibody the subject's immune system is induced to kill the tumor cell. The antibodies useful in the ADCC procedure include antibodies which interact with a cell in the body. Many such antibodies specific for cellular targets have been described in the art and many are commercially available. The nucleic acids when used in combination with monoclonal antibodies serve to reduce the dose of the antibody required to achieve a biological result.

In one embodiment of the present invention the anti-cancer agent used in conjunction with the immunostimulatory nucleic acids and pharmaceutical compositions described herein is an anti-angiogenesis agent (e.g., an agent that stops tumors from developing new blood vessels). Examples of anti-angiogenesis agents include VEGF inhibitors, VEGFR inhibitors, TIE-2 inhibitors, PDGFR inhibitors, angiopoietin inhibitors, PKC$\beta$ inhibitors, COX-2 (cyclooxygenase II) inhibitors, integrins (alpha-v/beta-3), MMP-2 (matrix-metalloproteinase 2) inhibitors, and MMP-9 (matrix-metalloproteinase 9) inhibitors.

Preferred anti-angiogenesis agents include sunitinib (Sutent™), bevacizumab (Avastin™), axitinib (AG 13736), SU 14813 (Pfizer), and AG 13958 (Pfizer).

Additional anti-angiogenesis agents include vatalanib (CGP 79787), Sorafenib (Nexavar™), pegaptanib octasodium (Macugen™), vandetanib (Zactima™), PF-0337210 (Pfizer), SU 14843 (Pfizer), AZD 2171 (AstraZeneca), ranibizumab (Lucentis™), Neovastat™ (AE 941), tetrathiomolybdata (Coprexa™), AMG 706 (Amgen), VEGF Trap (AVE 0005), CEP 7055 (Sanofi-Aventis), XL 880 (Exelixis), telatinib (BAY 57-9352), and CP-868,596 (Pfizer).

Other anti-angiogenesis agents include enzastaurin (LY 317615), midostaurin (CGP 41251), perifosine (KRX 0401), teprenone (Selbex™) and UCN 01 (Kyowa Hakko).

Other examples of anti-angiogenesis agents which can be used in conjunction with a the immunostimulatory nucleic acids and pharmaceutical compositions described herein include celecoxib (Celebrex™), parecoxib (Dynastat™), deracoxib (SC 59046), lumiracoxib (Preige™), valdecoxib (Bextra™), rofecoxib (Vioxx™), iguratimod (Careram™), IP 751 (Invedus), SC-58125 (Pharmacia) and etoricoxib (Arcoxia™).

Other anti-angiogenesis agents include exisulind (Aptosyn™), salsalate (Amigesic™), diflunisal (Dolobid™), ibuprofen (Motrin™), ketoprofen (Orudis™), nabumetone (Relafen™), piroxicam (Feldene™), naproxen (Aleve™, Naprosyn™), diclofenac (Voltaren™), indomethacin (Indocin™), sulindac (Clinoril™), tolmetin (Tolectin™), etodolac (Lodine™), ketorolac (Toradol™), and oxaprozin (Daypro™).

Other anti-angiogenesis agents include ABT 510 (Abbott), apratastat (TMI 005), AZD 8955 (AstraZeneca), incyclinide (Metastat™), and PCK 3145 (Procyon).

Other anti-angiogenesis agents include acitretin (Neotigason™), plitidepsin (Aplidine™), cilengtide (EMD 121974), combretastatin A4 (CA4P), fenretinide (4 HPR), halofuginone (Tempostatin™), Panzem™ (2-methoxyestradiol), PF-03446962 (Pfizer), rebimastat (BMS 275291), catumaxomab (Removab™), lenalidomide (Revlimid™), squalamine (EVIZON™), thalidomide (Thalomid™), Ukrain™ (NSC 631570), Vitaxin™ (MEDI 522), and zoledronic acid (Zometa™).

In another embodiment, the anti-cancer agent is a so-called signal transduction inhibitor (e.g., inhibiting the means by which regulatory molecules that govern the fundamental processes of cell growth, differentiation, and survival communicate within the cell). Signal transduction inhibitors include small molecules, antibodies, and antisense molecules. Signal transduction inhibitors include, for example, kinase inhibitors (e.g., tyrosine kinase inhibitors or serine/threonine kinase inhibitors) and cell cycle inhibitors. More specifically, signal transduction inhibitors include, for example, farnesyl protein transferase inhibitors, EGF inhibitor, ErbB-1 (EGFR), ErbB-2, pan erb, IGF1R inhibitors, MEK, c-Kit inhibitors, FLT-3 inhibitors, K-Ras inhibitors, PI3 kinase inhibitors, JAK inhibitors, STAT inhibitors, Raf kinase inhibitors, Akt inhibitors, mTOR inhibitors, P70S6 kinase inhibitors, inhibitors of the WNT pathway and so called multi-targeted kinase inhibitors.

Preferred signal transduction inhibitors include gefitinib (Iressa™), cetuximab (Erbitux™), erlotinib (Tarceva™), trastuzumab (Herceptin™), sunitinib (Sutent™), imatinib (Gleevec™), and PD325901 (Pfizer).

Additional examples of signal transduction inhibitors, which may be used in conjunction with the immunostimulatory nucleic acids and pharmaceutical compositions described herein, include BMS 214662 (Bristol-Myers Squibb), Ionafarnib (Sarasar™), pelitrexol (AG 2037), matuzumab (EMD 7200), nimotuzumab (TheraCIM h-R3™), panitumumab (Vectibix™), Vandetanib (Zactima™), pazopanib (SB 786034), ALT 110 (Alteris Therapeutics), BIBW 2992 (Boehringer Ingelheim), and Cervene™ (TP 38).

Other examples of signal transduction inhibitors include PF-2341066 (Pfizer), PF-299804 (Pfizer), canertinib (CI 1033), pertuzumab (Omnitarg™), Lapatinib (Tycerb™), pelitinib (EKB 569), miltefosine (Miltefosin™), BMS 599626 (Bristol-Myers Squibb), Lapuleucel-T (Neuvenge™), NeuVax™ (E75 cancer vaccine), Osidern™ (IDM 1), mubritinib (TAK-165), CP-724,714 (Pfizer), and panitumumab (Vectibix™).

Other examples of signal transduction inhibitors include ARRY 142886 (Array Biopharm), everolimus (Certican™), zotarolimus (Endeavor™), temsirolimus (Torisel™), AP 23573 (ARIAD), and VX 680 (Vertex).

Additionally, other signal transduction inhibitors include XL 647 (Exelixis), sorafenib (Nexavar™), LE-AON (Georgetown University), and GI-4000 (Globelmmune).

Other signal transduction inhibitors include ABT 751 (Abbott), alvocidib (flavopiridol), BMS 387032 (Bristol Myers), EM 1421 (Erimos), indisulam (E 7070), seliciclib (CYC 200), BIO 112 (One Bio), BMS 387032 (Bristol-Myers Squibb), PD 0332991 (Pfizer), and AG 024322 (Pfizer).

This invention contemplates the use of an immunostimulatory nucleic acid described herein together with classical antineoplastic agents. Classical antineoplastic agents include, but are not limited to, hormonal modulators such as hormonal, anti-hormonal, androgen agonist, androgen antagonist and anti-estrogen therapeutic agents, histone deacetylase (HDAC) inhibitors, gene silencing agents or gene activating agents, ribonucleases, proteosomics, Topoisomerase I inhibitors, Camptothecin derivatives, Topoisomerase II inhibitors, alkylating agents, antimetabolites, poly(ADP-ribose) polymerase-1 (PARP-1) inhibitors, microtubulin inhibitors, antibiotics, plant derived spindle inhibitors, platinum-coordinated compounds, gene therapeutic agents, antisense oligonucleotides, vascular targeting agents (VTAs), and statins.

Examples of classical antineoplastic agents used in combination therapy with a the immunostimulatory nucleic acid described herein, optionally with one or more other agents include, but are not limited to, glucocorticoids, such as dexamethasone, prednisone, prednisolone, methylprednisolone, hydrocortisone, and progestins such as medroxyprogesterone, megestrol acetate (Megace), mifepristone (RU-486), Selective Estrogen Receptor Modulators (SERMs, such as tamoxifen, raloxifene, lasofoxifene, afimoxifene, arzoxifene, bazedoxifene, fispemifene, ormeloxifene, ospemifene, tesmilifene, toremifene, trilostane and CHF 4227 (Cheisi)), Selective Estrogen-Receptor Downregulators (SERDs, such as fulvestrant), exemestane (Aromasin), anastrozole (Arimidex), atamestane, fadrozole, letrozole (Femara), gonadotropin-releasing hormone (GnRH) agonists, which are commonly referred to as luteinizing hormone-releasing hormone (LHRH) agonists, such as buserelin (Suprefact), goserelin (Zoladex), leuprorelin (Lupron), triptorelin (Trelstar), abarelix (Plenaxis), bicalutamide (Casodex), cyproterone, flutamide (Eulexin), megestrol, nilutamide (Nilandron), osaterone, dutasteride, epristeride, finasteride, Serenoa repens, PHL 00801, abarelix, goserelin, leuprorelin, triptorelin, bicalutamide, tamoxifen, exemestane, anastrozole, fadrozole, formestane, and letrozole, and combinations thereof.

Other examples of classical antineoplastic agents used in combination with the immunostimulatory nucleic acids described herein include, but are not limited to, suberolanilide hydroxamic acid (SAHA, Merck Inc./Aton Pharmaceuticals), depsipeptide (FR901228 or FK228), G2M-777, MS-275, pivaloyloxymethyl butyrate and PXD-101; Onconase (ranpirnase), PS-341 (MLN-341), Velcade (bortezomib), belotecan, BN-80915 (Roche), camptothecin, diflomotecan, edotecarin, exatecan (Daiichi), gimatecan, irinotecan HCl (Camptosar), lurtotecan, Orathecin (rubitecan, Supergen), SN-38, topotecan, camptothecin, 10-hydroxycamptothecin, 9-aminocamptothecin, irinotecan, SN-38, edotecarin, topotecan, aclarubicin, adriamycin, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, taflupuside, valrubicin, Zinecard (dexrazoxane), nitrogen mustard N-oxide, cyclophosphamide, AMD-473, altretamine, AP-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating compounds such as cisplatin, Paraplatin (carboplatin), eptaplatin, lobaplatin, nedaplatin, Eloxatin (oxaliplatin, Sanofi), streptozocin, satrplatin, and combinations thereof.

The invention also contemplates the use of the compounds the immunostimulatory nucleic acids described herein together with dihydrofolate reductase inhibitors (such as methotrexate and Neu Trexin (trimetresate glucuronate)), purine antagonists (such as 6-mercaptopurine riboside, mercaptopurine, 6-thioguanine, cladribine, clofarabine (Clolar), fludarabine, nelarabine, and raltitrexed), pyrimidine antagonists (such as 5-fluorouracil (5-FU)), Alimta (premetrexed disodium, LY231514, MTA), capecitabine (Xeloda™), cytosine arabinoside, Gemzar™ (gemcitabine, Eli Lilly), Tegafur (UFT Orzel or Uforal and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynylcytidine) and other antimetabolites such as eflornithine, hydroxyurea, leucovorin, nolatrexed (Thymitaq), triapine, trimetrexate, N-(5-[N-(3,4-dihydro-2-methyl-4-oxoquinazolin-6-ylmethyl)-N-methylamino]-2-thenoyl)-L-glutamic acid, AG-014699 (Pfizer Inc.), ABT-472 (Abbott Laboratories), INO-1001 (Inotek Pharmaceuticals), KU-0687 (KuDOS Pharmaceuticals) and GPI 18180 (Guilford Pharm Inc) and combinations thereof.

Other examples of classical antineoplastic cytotoxic agents used in combination therapy with the immunostimulatory nucleic acids described herein, optionally with one or more other agents include, but are not limited to, Abraxane (Abraxis BioScience, Inc.), Batabulin (Amgen), EPO 906 (Novartis), Vinflunine (Bristol-Myers Squibb Company), actinomycin D, bleomycin, mitomycin C, neocarzinostatin (Zinostatin), vinblastine, vincristine, vindesine, vinorelbine (Navelbine), docetaxel (Taxotere), Ortataxel, paclitaxel (including Taxoprexin a DHA/paclitaxel conjugate), cisplatin, carboplatin, Nedaplatin, oxaliplatin (Eloxatin), Satraplatin, Camptosar, capecitabine (Xeloda), oxaliplatin (Eloxatin), Taxotere alitretinoin, Canfosfamide (Telcyta™), DMXAA (Antisoma), ibandronic acid, L-asparaginase, pegaspargase (Oncaspar™), Efaproxiral (Efaproxyn™—radiation therapy), bexarotene (Targretin™), Tesmilifene (DPPE—enhances efficacy of cytotoxics), Theratope™ (Biomira), Tretinoin (Vesanoid™), tirapazamine (Trizaone™), motexafin gadolinium (Xcytrin™), Cotara™ (mAb), NBI-3001 (Protox Therapeutics), polyglutamate-paclitaxel (Xyotax™) and combinations thereof.

Further examples of classical antineoplastic agents used in combination therapy with the immunostimulatory nucleic acids described herein, optionally with one or more other agents include, but are not limited to, as Advexin (ING 201), TNFerade (GeneVec, a compound which expresses TNFalpha in response to radiotherapy), RB94 (Baylor College of Medicine), Genasense (Oblimersen, Genta), Combretastatin A4P (CA4P), Oxi-4503, AVE-8062, ZD-6126, TZT-1027, Atorvastatin (Lipitor, Pfizer Inc.), Provastatin (Pravachol, Bristol-Myers Squibb), Lovastatin (Mevacor, Merck Inc.), Simvastatin (Zocor, Merck Inc.), Fluvastatin (Lescol, Novartis), Cerivastatin (Baycol, Bayer), Rosuvastatin (Crestor, AstraZeneca), Lovastatin, Niacin (Advicor, Kos Pharmaceuticals), Caduet, Lipitor, torcetrapib, and combinations thereof.

Another embodiment of the present invention relates to a method for the treatment of breast cancer in a human in need of such treatment, comprising administering to said human an amount of an immunostimulatory nucleic acid described herein, in combination with one or more (preferably one to three) anti-cancer agents selected from the group consisting of trastuzumab, tamoxifen, docetaxel, paclitaxel, capecitabine, gemcitabine, vinorelbine, exemestane, letrozole and anastrozole.

In one embodiment the invention provides a method of treating colorectal cancer in a mammal, such as a human, in need of such treatment, by administering an amount of an immunostimulatory nucleic acid described herein, in combination with one or more (preferably one to three) anti-cancer agents. Examples of particular anti-cancer agents include those typically used in adjuvant chemotherapy, such as FOL-FOX, a combination of 5-fluorouracil (5-FU) or capecitabine (Xeloda), leucovorin and oxaliplatin (Eloxatin). Further examples of particular anti-cancer agents include those typically used in chemotherapy for metastatic disease, such as FOLFOX or FOLFOX in combination with bevacizumab (Avastin); and FOLFIRI, a combination of 5-FU or capecitabine, leucovorin and irinotecan (Camptosar). Further examples include 17-DMAG, ABX-EFR, AMG-706, AMT-2003, ANX-510 (CoFactor), aplidine (plitidepsin, Aplidin), Aroplatin, axitinib (AG-13736), AZD-0530, AZD-2171, *bacillus* Calmette-Guerin (BCG), bevacizumab (Avastin), BIO-117, BIO-145, BMS-184476, BMS-275183, BMS-528664, bortezomib (Velcade), C-1311 (Symadex), cantuzumab mertansine, capecitabine (Xeloda), cetuximab (Erbitux), clofarabine (Clofarex), CMD-193, combretastatin, Cotara, CT-2106, CV-247, decitabine (Dacogen), E-7070, E-7820, edotecarin, EMD-273066, enzastaurin (LY-317615) epothilone B (EPO-906), erlotinib (Tarceva), flavopyridol, GCAN-101, gefitinib (Iressa), huA33, huC242-DM4, imatinib (Gleevec), indisulam, ING-1, irinotecan (CPT-11, Camptosar) ISIS 2503, ixabepilone, lapatinib (Tykerb), mapatumumab (HGS-ETR1), MBT-0206, MEDI-522 (Abregrin), Mitomycin, MK-0457 (VX-680), MLN-8054, NB-1011, NGR-TNF, NV-1020, oblimersen (Genasense, G3139), OncoVex, ONYX 015 (CI-1042), oxaliplatin (Eloxatin), panitumumab (ABX-EGF, Vectibix), pelitinib (EKB-569), pemetrexed (Alimta), PD-325901, PF-0337210, PF-2341066, RAD-001 (Everolimus), RAV-12, Resveratrol, Rexin-G, S-1 (TS-1), seliciclib, SN-38 liposome, Sodium stibogluconate (SSG), sorafenib (Nexavar), SU-14813, sunitinib (Sutent), temsirolimus (CCI 779), tetrathiomolybdate, thalomide, TLK-286 (Telcyta), topotecan (Hycamtin), trabectedin (Yondelis), vatalanib (PTK-787), vorinostat (SAHA, Zolinza), WX-UK1, and ZYC300, wherein the amounts of the active agent together with the amounts of the combination anticancer agents are effective in treating colorectal cancer.

Another embodiment relates to a method for the treatment of renal cell carcinoma in a human in need of such treatment, comprising administering to said human an amount of an immunostimulatory nucleic acid described herein, in combination with one or more (preferably one to three) anti-cancer agents selected from the group consisting of capecitabine (Xeloda), interferon alpha, interleukin-2, bevacizumab (Avastin), gemcitabine (Gemzar), thalidomide, cetuximab (Erbitux), vatalanib (PTK-787), Sutent, AG-13736, SU-11248, Tarceva, Iressa, Lapatinib and Gleevec, wherein the amounts of the active agent together with the amounts of the combination anticancer agents is effective in treating renal cell carcinoma.

Another embodiment relates to a method for the treatment of melanoma in a human in need of such treatment, comprising administering to said human an amount of a immunostimulatory nucleic acid described herein, in combination with one or more (preferably one to three) anti-cancer agents selected from the group consisting of interferon alpha, interleukin-2, temozolomide (Temodar), docetaxel (Taxotere), paclitaxel, Dacarbazine (DTIC), carmustine (also known as BCNU), Cisplatin, vinblastine, tamoxifen, PD-325,901, Axitinib, bevacizumab (Avastin), thalidomide, sorafanib, vatalanib (PTK-787), Sutent, CpG-7909, AG-13736, Iressa, Lapatinib and Gleevec, wherein the amounts of the active agent together with the amounts of the combination anticancer agents is effective in treating melanoma.

Another embodiment of the present invention of particular interest relates to a method for the treatment of lung cancer in a human in need of such treatment, comprising administering to said human an amount of an immunostimulatory nucleic acid described herein, in combination with one or more (preferably one to three) anti-cancer agents selected from the group consisting of capecitabine (Xeloda), bevacizumab (Avastin), gemcitabine (Gemzar), docetaxel (Taxotere), paclitaxel, premetrexed disodium (Alimta), Tarceva, Iressa, Vinorelbine, Irinotecan, Etoposide, Vinblastine, and Paraplatin (carboplatin), wherein the amounts of the active agent together with the amounts of the combination anticancer agents is effective in treating Lung cancer.

Cancer vaccines are medicaments which are intended to stimulate an endogenous immune response against cancer cells. Currently produced vaccines predominantly activate the humoral immune system (i.e., the antibody dependent immune response). Other vaccines currently in development are focused on activating the cell-mediated immune system including cytotoxic T lymphocytes which are capable of killing tumor cells. Cancer vaccines generally enhance the presentation of cancer antigens to both antigen presenting cells (e.g., macrophages and dendritic cells) and/or to other immune cells such as T cells, B cells, and NK cells. In some instances, cancer vaccines may be used along with adjuvants, such as those described above.

Some cancer cells are antigenic and thus can be targeted by the immune system. The combined administration of an immunostimulatory nucleic acid and a cancer medicament, particularly those which are classified as cancer immunotherapies, is useful for stimulating a specific immune response against a cancer antigen. The terms "cancer antigen" and "tumor antigen" are used interchangeably to refer to antigens which are differentially expressed by cancer cells and can, therefore, be exploited to target cancer cells.

Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation, and those that are temporally expressed such as embryonic and fetal antigens. Other cancer antigens are encoded by mutant cellular genes, such as oncogenes (e.g., activated ras oncogene), suppressor genes (e.g., mutant p53), and oncogenic fusion proteins resulting from internal deletions or chromosomal translocations. Still other cancer antigens can be encoded by viral genes such as those carried on RNA and DNA tumor viruses. "Tumor-associated" antigens are present in both tumor cells and normal cells, but are present in a different quantity or a different form in tumor cells. Examples of such antigens are oncofetal antigens (e.g., carcinoembryonic antigen), differentiation antigens (e.g., T and Tn antigens), oncogene products (e.g., HER/neu). Cancer antigens, such as those present in cancer vaccines or those used to prepare cancer immunotherapies, can be prepared from crude cancer cell extracts, as described in Cohen, P A et al. (1994) *Cancer Res* 54(4):1055-58, or by partially purifying the antigens, using recombinant technology, or de novo synthesis of known antigens.

Cancer antigens can be used in the form of immunogenic portions of a particular antigen or in some instances a whole cell or a tumor mass can be used as the antigen. Such antigens can be isolated or prepared recombinantly or by any other means known in the art.

Other vaccines take the form of dendritic cells which have been exposed to cancer antigens in vitro, have processed the antigens, and are able to express the cancer antigens at their cell surface in the context of major histocompatibility complex (MHC) molecules, for effective antigen presentation to other immune system cells. Dendritic cells form the link between the innate and the acquired immune system through their presentation of antigens and their expression of pattern recognition receptors which detect microbial molecules like lipopolysaccharides (LPS) in their local environment.

The disclosed immunostimulatory nucleic acids are useful for the treatment of allergy, including asthma. The immunostimulatory nucleic acids can be used, either alone or in combination with an allergy/asthma medicament, to treat allergy. The method entails administering to a subject having or at risk of developing an allergic or asthmatic condition an effective amount of an immunostimulatory nucleic acid of the invention to treat the allergic or asthmatic condition.

As used herein, "allergy" refers to acquired hypersensitivity to a substance (allergen). Allergic conditions include eczema, allergic rhinitis or coryza, hay fever, asthma, urticaria (hives) and food allergies, and other atopic conditions. A "subject having an allergy" is a subject that has or is at risk of developing an allergic reaction in response to an allergen. An "allergen" refers to a substance that can induce an allergic or asthmatic response in a susceptible subject. The list of allergens is enormous and can include pollens, insect venoms, animal dander, dust, fungal spores and drugs (e.g., penicillin).

Examples of natural animal and plant allergens include proteins specific to the following genera: *Canine* (*Canis familiaris*); *Dermatophagoides* (e.g., *Dermatophagoides farinae*); *Felis* (*Felis domesticus*); *Ambrosia* (*Ambrosia artemiisfolia*); *Lolium* (e.g., *Lolium perenne* or *Lolium multiflorum*); *Cryptomeria* (*Cryptomeria japonica*); *Alternaria* (*Alternaria alternata*); *Alder; Alnus* (*Alnus gultinosa*); *Betula* (*Betula verrucosa*); *Quercus* (*Quercualba*); *Olea* (*Olea europa*); *Artemisia* (*Artemisia vulgaris*); *Plantago* (e.g., *Planlago lanceolata*); *Parietaria* (e.g., *Parietaria officinalis* or *Parietaria judaica*); *Blattella* (e.g., *Blattella germanica*); *Apis* (e.g., *dpis multiflorum*); *Cupressus* (e.g., *Cupressus sempervirens, Cupressus arizonica* and *Cupressus macrocarpa*); *Juniperus* (e.g., *Juniperus sabinoide, Juniperus virginiana, Juniperus communis* and *Juniperus ashei*); *Thuya* (e.g., *Thuy orientalis*); *Chamaecyparis* (e.g., *Chamaecyparis obtusa*); *Periplaneta* (e.g., *Periplaneta americana*); *Agropyron* (e.g., *Agropyron repens*); *Secale* (e.g., *Secale cereale*); *Triticum* (e.g., *Triticum aestivum*); *Dactylis* (e.g., *Dactylis glomerata*); *Festuca* (e.g., *Fesluca elatior*); *Poa* (e.g., *Poa pratensis* or *Poa compressa*); *Arena* (e.g., *Arena sativa*); *Holcus* (e.g. *Holcus lanatus*); *Anthoxanthum* (e.g., *Anthoxanthum odoratum*); *Arrhenatherum* (e.g., *Arrhenatherum elatius*); *Agrostis* (e.g., *Agrostis alba*); *Phleum* (e.g., *Phleum pratense*); *Phalaris* (e.g., *Phalaris arundinacea*); *Paspalum* (e.g., *Paspalum notatum*); *Sorghum* (e.g., *Sorghum halepensis*); and *Bromus* (e.g., *Bromus inermis*).

As used herein, "asthma" refers to a disorder of the respiratory system characterized by inflammation, narrowing of the airways and increased reactivity of the airways to inhaled agents. Asthma is frequently, although not exclusively, associated with atopic or allergic symptoms.

An "asthma/allergy medicament," as used herein, is a composition of matter which reduces the symptoms, inhibits the asthmatic or allergic reaction, or prevents the development of an allergic or asthmatic reaction. Various types of medicaments for the treatment of asthma and allergy are described in the "Guidelines for the Diagnosis and Management of Asthma," Expert Panel Report 2, NIH Publication No. 97/4051 (Jul. 19, 1997), the entire contents of which are incorporated herein by reference. The summary of the medicaments as described in the NIH publication is presented below.

In most embodiments the asthma/allergy medicament is useful to some degree for treating both asthma and allergy. Some asthma/allergy medicaments are preferably used in combination with the immunostimulatory nucleic acids to treat asthma. These are referred to as asthma medicaments. Asthma medicaments include, but are not limited to, PDE-4 inhibitors, bronchodilator/beta-2 agonists, K+ channel openers, VLA-4 antagonists, neurokin antagonists, TXA2 synthesis inhibitors, xanthanines, arachidonic acid antagonists, lipoxygenase inhibitors, thromboxin A2 receptor antagonists, thromboxane A2 antagonists, inhibitor of 5-lipoxygenase activation proteins, and protease inhibitors.

Other asthma/allergy medicaments are preferably used in combination with the immunostimulatory nucleic acids to treat allergy. These are referred to as allergy medicaments. Allergy medicaments include, but are not limited to, antihistamines, steroids, immunomodulators, and prostaglandin inducers. Antihistamines are compounds which counteract histamine released by mast cells or basophils. These compounds are well known in the art and commonly used for the treatment of allergy. Antihistamines include, but are not limited to, loratidine, cetirizine, buclizine, ceterizine analogues, fexofenadine, terfenadine, desloratadine, norastemizole, epinastine, ebastine, ebastini, astemizole, levocabastine, azelastine, tranilast, terfenadine, mizolastine, betatastine, CS 560, and HSR10 609. Prostaglandin inducers are compounds which induce prostaglandin activity. Prostaglandins function by regulating smooth muscle relaxation. Prostaglandin inducers include, but are not limited to, S-5751.

The steroids include, but are not limited to, beclomethasone, fluticasone, tramcinolone, budesonide, corticosteroids and budesonide. The combination of immunostimulatory nucleic acids and steroids are particularly well suited to the treatment of young subjects (e.g., children). To date, the use of steroids in children has been limited by the observation that some steroid treatments have been reportedly associated with growth retardation. Thus, according to the present invention, the immunostimulatory nucleic acids can be used in combination with growth retarding steroids, and can thereby provide a "steroid sparing effect." The combination of the two agents can result in lower required doses of steroids.

The immunomodulators include, but are not limited to, the group consisting of anti-inflammatory agents, leukotriene antagonists, IL-4 muteins, soluble IL-4 receptors, immunosuppressants (such as tolerizing peptide vaccine), anti-IL-4 antibodies, IL-4 antagonists, anti-IL-5 antibodies, soluble IL-13 receptor-Fc fusion proteins, anti-IL-9 antibodies, CCR3 antagonists, CCR5 antagonists, VLA-4 inhibitors, and down regulators of IgE.

The immunostimulatory nucleic acids of the invention can be used to induce type 1 IFN, i.e., IFN-α and IFN-β. The method involves contacting a cell capable of expressing a type 1 IFN with an effective amount of an immunostimulatory nucleic acid of the invention to induce type 1 IFN expression by the cell. It has recently been appreciated that the major producer cell type of IFN-α in humans is the plasmacytoid dendritic cell (pDC). This type of cell occurs at very low frequency (0.2-0.4 percent) in PBMC and is characterized by a phenotype that is lineage negative (i.e., does not stain for CD3, CD14, CD19, or CD56) and is CDIIc negative, while positive for CD4, CD123 (IL-3Rα), and class II major histocompatibility complex (MHC class II). See Grouard, G et al. (1997) *J Exp Med* 5 185:1101-11; Rissoan, M-C et al. (1999) *Science* 283:1183-86; Siegal, F P et al. (1999) *Science* 284: 1835-37; and Celia, M et al. (1999) *Nat Med* 5:919-23. Methods of measuring type 1 IFN are well known by those skilled in the art, and they include, for example, enzyme-linked immunosorbent assay (ELISA), bioassay, and fluorescence-activated cell sorting (FACS). Assays of this sort can be performed using readily available commercial reagents and kits.

The immunostimulatory nucleic acids of the invention may be used to activate NK cells. The method involves contacting an NK cell with an effective amount of an immunostimulatory nucleic acid of the invention to activate the NK cell. The activation of the NK cells may be direct activation or indirect activation. Indirect activation refers to the induction of cytokines or other factors which cause the subsequent activation of the NK cells. NK cell activation can be assessed by various methods, including measuring lytic activity, measuring the induction of activation markers, such as CD69, or measuring the induction of certain cytokines. In addition to their characteristic ability to kill certain tumor targets spontaneously, NK cells participate in ADCC and are major producers of IFN-γ, TNF-α, GM-CSF and IL-3.

The prototypical NK-sensitive cell target for mouse NK cells is yeast artificial chromosome (YAC)-I, which is a thymoma derived from Moloney virus-infected A strain mice. For human NK cells, a standard target is K562, which is a cell line derived from an erythroleukemic lineage. In microtiter plates, a constant number of radiolabeled targets (e.g., $^{51}$Cr-labeled K562) is incubated either alone (spontaneous), with detergent (maximum), or with varying numbers of effector cells (experimental). The ratio of effector to target cells is referred to the E:T ratio. Enriched, activated NK cells typically are effective at E:T ratios of less than 10:1, while unfractionated PBMCs or splenocytes require E:T ratios of 100:1 or more.

The immunostimulatory nucleic acids also are useful as adjuvants for inducing a systemic and/or mucosal immune response. The immunostimulatory nucleic acid of the invention can be delivered to a subject exposed to an antigen to produce an enhanced immune response to the antigen. Thus, for example, the immunostimulatory nucleic acids described herein are useful as vaccine adjuvants.

The immunostimulatory nucleic acids may be administered in combination with non-nucleic acid adjuvants. A non-nucleic acid adjuvant is any molecule or compound, except for the immunostimulatory nucleic acids described herein, which can stimulate the humoral and/or cellular immune response. Non-nucleic acid adjuvants include, for instance, adjuvants that create a depot effect, immune stimulating adjuvants, and adjuvants that create a depot effect and stimulate the immune system. A non-nucleic acid mucosal adjuvant as used herein is an adjuvant other than an immunostimulatory nucleic acid that is capable of inducing a mucosal immune response in a subject when administered to a mucosal surface in conjunction with an antigen.

The immunostimulatory nucleic acids of the invention may be formulated as pharmaceutical compositions in a pharmaceutically acceptable carrier. The immunostimulatory nucleic acids may be directly administered to the subject or may be administered in conjunction with a nucleic acid delivery complex. A nucleic acid delivery complex refers to a nucleic acid molecule associated with (e.g., ionically bound to, covalently bound to, or encapsulated within) a targeting means (e.g., a molecule that results in higher affinity binding to target cell (e.g., B-cell surfaces) and/or increased cellular uptake by target cells). Examples of nucleic acid delivery complexes include nucleic acids associated with a sterol (e.g., cholesterol), a lipid (e.g., a cationic lipid, virosome or liposome), or a target specific binding agent (e.g., a ligand recognized by target cell specific receptor). Preferred complexes may be sufficiently stable in vivo to prevent significant uncoupling prior to internalization by the target cell. However, the complex can be cleavable under appropriate conditions within the cell so that the nucleic acid is released in a functional form.

The immunostimulatory nucleic acid and/or the antigen and/or other therapeutics may be administered alone (e.g., in saline or buffer) or using any delivery vehicles known in the art. For instance the following delivery vehicles have been described: cochleates, emulsomes, immunostimulating complexes (ISCOMs), liposomes, microspheres, polymers (e.g., carboxymethylcellulose, chitosan), polymer rings, proteosomes, virosomes, virus-like particles, and other delivery vehicles.

Suitable dosages of the immunostimulatory nucleic acids described herein for mucosal or local delivery to a subject typically range from about 0.1 µg to about 10 mg per administration, which depending on the application could be given daily, weekly, or monthly and any other amount of time there between. More typically, mucosal or local doses range from about 10 µg to about 5 mg per administration, or from about 100 µg to about 1 mg, with 2-4 administrations being spaced days or weeks apart. Typically, immune stimulant doses range from 1 µg to 10 mg per administration, and from about 10 µg to about 1 mg, with daily or weekly administrations. Dosages of the compounds described herein for parenteral delivery for the purpose of inducing an antigen-specific immune response in a subject, in which the compounds are delivered with an antigen but not another therapeutic agent, are typically 5 to 10,000 times higher than the effective mucosal dose for vaccine adjuvant or immune stimulant applications, or 10 to 1,000 times higher, or 20 to 100 times higher. Dosages of the compounds described herein for parenteral delivery for the purpose of inducing an innate immune response or for increasing ADCC or for inducing an antigen specific immune response when the immunostimulatory nucleic acids are administered in combination with other therapeutic agents or in specialized delivery vehicles typically range from about 0.1 µg to 10 mg per administration, which depending on the application could be given daily, weekly, or monthly and any other amount of time there between. More typically, parenteral doses for these purposes range from about 10 µg to 5 mg per administration, or from about 100 µg to 1 mg, with 2-4 administrations being spaced days or weeks apart. In some embodiments, however, parenteral doses for these purposes may be used in a range that is 5 to 10,000 times higher than the doses described above.

As used herein, "effective amount" refers to the amount necessary or sufficient to realize a desired biological effect. For example, an effective amount of an immunostimulatory nucleic acid for treating an infection is that amount necessary to treat the infection. Combined with the teachings provided herein, by choosing among the various active compounds and weighing factors such as potency, relative bioavailability, subject body weight, severity of adverse side-effects and preferred mode of administration, an effective prophylactic or therapeutic treatment regimen can be planned which does not cause substantial toxicity and yet is effective to treat the particular subject. The effective amount for any particular application can vary depending on such factors as the disease or condition being treated, the particular immunostimulatory nucleic acid being administered, the antigen, the size of the subject, or the severity of the disease or condition. One of ordinary skill in the art can empirically determine the effective amount of a particular immunostimulatory nucleic acid and/or antigen and/or other therapeutic agent without necessitating undue experimentation. For any compound described herein the therapeutically effective amount can be initially determined from animal models. A therapeutically effective dose can also be determined from human data for CpG oligonucleotides which have been tested in humans and for compounds which are known to exhibit similar pharmacological activities, such as other mucosal adjuvants, e.g., LT and other antigens for vaccination purposes, for the mucosal or local administration. Higher doses are required for parenteral administration. The applied dose can be adjusted based on the relative bioavailability and potency of the administered compound. Adjusting the dose to achieve maximal efficacy based on the methods described above and other methods known in the art, is well within the capabilities of the ordinarily skilled artisan.

The formulations of the invention may be administered in pharmaceutically acceptable solutions, which may routinely contain pharmaceutically acceptable concentrations of salt, buffering agents, preservatives, compatible carriers, adjuvants, and optionally other therapeutic ingredients. For use in therapy, an effective amount of the immunostimulatory nucleic acid can be administered to a subject by any mode that delivers the nucleic acid to the desired surface, e.g., mucosal, systemic. Administering the pharmaceutical composition of the present invention may be accomplished by any means known to the skilled artisan. Preferred routes of administration include, but are not limited to, oral, parenteral, intramuscular, intranasal, intratracheal, inhalation, ocular, sublingual, vaginal, and rectal. For oral administration, the compounds (i.e., immunostimulatory nucleic acids, and optional antigens and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose (HPMC), sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any pharmaceutical carders. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain processing agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, microcapsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer (1990) *Science* 249:1527-33, which is incorporated herein by reference.

The immunostimulatory nucleic acids and optionally other therapeutics and/or antigens may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, acid addition salts prepared from the following: hydrochloric, hydrobromic, sulfuric, nitric, phosphoric, maleic, acetic, salicylic, p-toluene sulfonic, tartaric, citric, methane sulfonic, formic, malonic, succinic, naphthalene-2-sulfonic, or benzene sulphonic acids. Also, such salts can be prepared as alkaline metal or alkaline earth salts, such as sodium, potassium or calcium base addition salts.

Suitable buffering agents include: acetic acid and a salt (1-2% w/v); citric acid and salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02%.

The pharmaceutical compositions of the invention contain an effective amount of an immunostimulatory nucleic acid and optionally antigens and/or other therapeutic agents optionally included in a pharmaceutically acceptable carrier. "Pharmaceutically acceptable" substances refers to those substances which are within the scope of sound medical judgment suitable for use in contact with the tissues of subjects without undue toxicity, irritation, allergic response, and so on, commensurate with a reasonable benefit-to-risk ratio, and effective for their intended use. The term "pharmaceutically acceptable carrier" thus means one or more compatible solid or liquid fillers, diluents or encapsulating substances which are suitable for administration to a human or other vertebrate animal. The term "carrier" denotes an organic or inorganic ingredient, natural or synthetic, with which the active ingredient is combined to facilitate the application to a subject. The components of the pharmaceutical compositions are also capable of being comingled with the compounds of the present invention, and with each other, in a manner such that there is no adverse interaction.

For treatment of a subject, depending on activity of the compound, manner of administration, purpose of the immunization (i.e., prophylactic or therapeutic), nature and severity of the disorder, age and body weight of the patient, different doses may be necessary.

The administration of a given dose can be carried out both by single administration in the form of an individual dose unit or else several smaller dose units. Multiple administrations of doses at specific intervals of weeks or months apart are usual for boosting the antigen-specific responses.

Other delivery systems can include time-release, delayed release or sustained release delivery systems. Such systems can avoid repeated administrations of the compounds, increasing convenience to the subject and the physician. Many types of release delivery systems are available and are known to those of ordinary skill in the art. They include polymer base systems, such as poly(lactide-glycolide), copolyoxalates, polycaprolactones, polyesteramides, polyorthoesters, polyhydroxybutyric acid, and polyanhydrides.

Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152; and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

The present invention is further illustrated by the following Examples, which should not be construed as limiting. The entire contents of all of the references (including literature references, issued patents, published patent applications, and co-pending patent applications) cited throughout this specification are hereby expressly incorporated by reference.

EXAMPLES

Various oligodeoxyribonucleotides (ODN) were prepared and their biological properties were evaluated in the examples, below. Their full-length sequences are represented by the following:

```
5' T*C_G*T*C*G*T*T*T*T*C*G*G*C*G*C*G*C*G*C*C*G*T 3';    (SEQ ID NO: 2)

5' T*C*G*T*C*G*T*T*T*T*C*G*G*C*G*C*G*C*G*C*C*G*T 3';    (SEQ ID NO: 3)

5' T*C*G*T*C*G*T*T*T*T*G*T*C*G*T*T*T*T*G*T*C*G*T*T 3';  (SEQ ID NO: 4)
and

5' T*G*C*T*G*C*T*T*T*T*G*T*G*C*T*T*T*T*G*T*G*C*T*T 3'.  (SEQ ID NO: 5)
```

For each of the oligodeoxyribonucleotides evaluated in these examples, the stabilized linkage (*) is a phosphorothioate linkage, the phosphodiester or phosphodiester-like linkage (_) is a phosphodiester linkage, and the 3' and 5' notations refer to the 3' and 5' ends of the oligodeoxyribonucleotide, respectively. For simplicity, the examples and figures use SEQ ID NOs to refer to specific ODN tested, though in general, other immunostimulatory oligonucleotides may have base sequences that include those given by SEQ ID NO: 2, SEQ ID NO: 3, etc.

Example 1

Human and Mouse TLR9 Signaling in Response to Oligonucleotides

HEK 293 cells were transfected with human and mouse TLR9 constructs to produce hTLR9-NFκB-293 cells and mTLR9-NFκB-293 cells, respectively. The cells were incubated with ODN having SEQ ID NO: 2, 3, and 4 for 16 hours. The cells were lysed and the signal was determined by luciferase readout.

Figure 1:
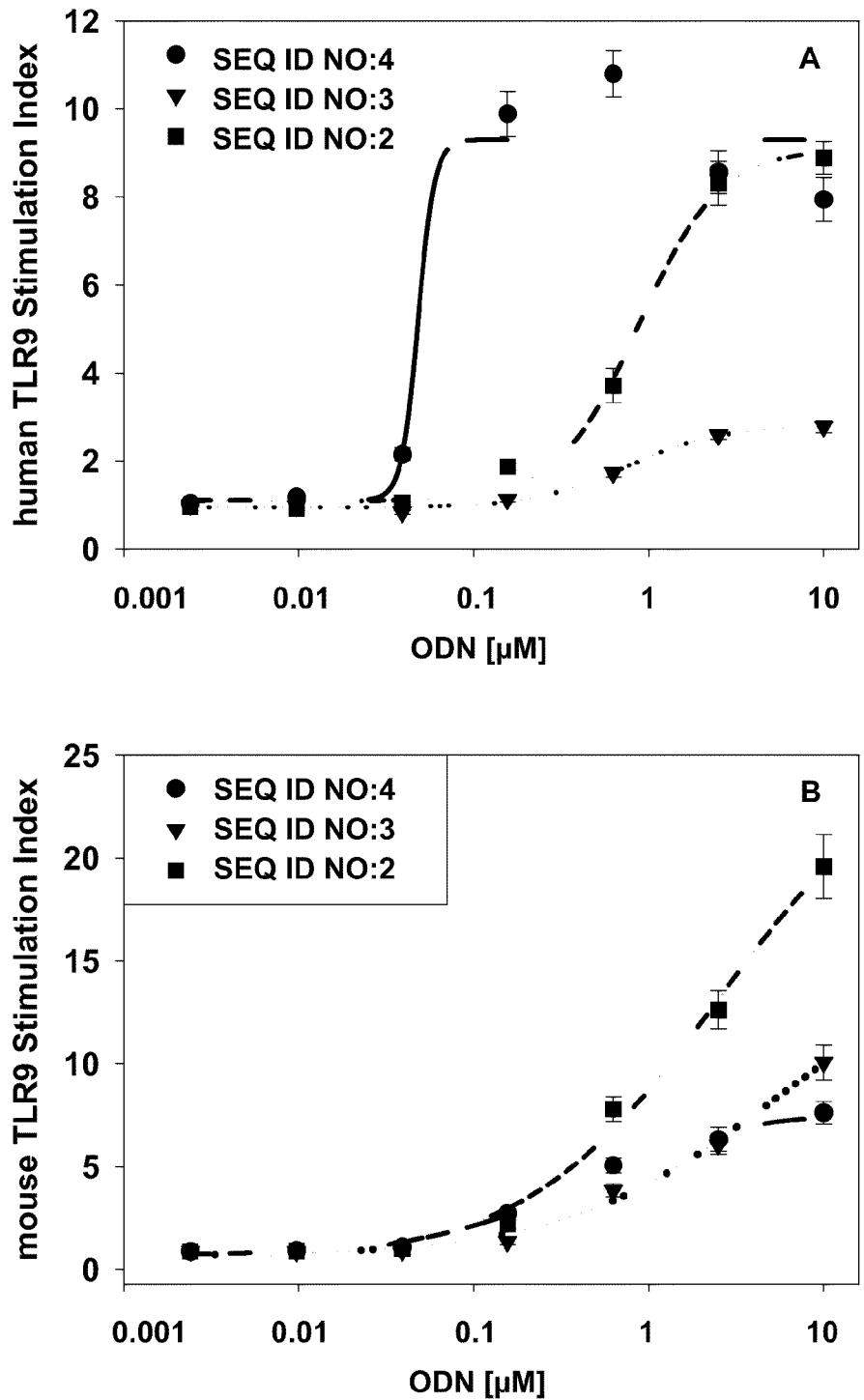
FIG. 1 is a set of graphs depicting human and mouse TLR9 reporter assays. Human TLR9 hTLR9-NFκB-293 cells were incubated with ODN in concentrations as indicated for 16 h, after which cells were lysed and luciferase activity was determined (FIG. 1 A). Mouse TLR9 mTLR9-NFκB-293 cells were incubated with ODN in concentrations as indicated for 16 h, after which cells were lysed and luciferase activity was determined (FIG. 1B).

The results are shown in FIG. 1. The EC50 was calculated using Sigma Plot (SigmaPlot 2002 for Windows version 8.0). All three ODN stimulated human TLR9.

Example 2

Responsiveness of pDC, PBMC, B Cells and NK Cells to Oligonucleotides

Levels of pDC, PBMC, B cell and NK cell activation following exposure of these cells to the CpG oligonucleotides are shown in FIG. 2-FIG. 9. As noted, above, the figures use SEQ ID NOs to refer to the specific oligonucleotides that were evaluated (SEQ ID NO: 2, 3, and 4). The molar concentration of oligonucleotide used to produce a particular data point is depicted along the X-axis (µM) of each graph.

Figure 2:
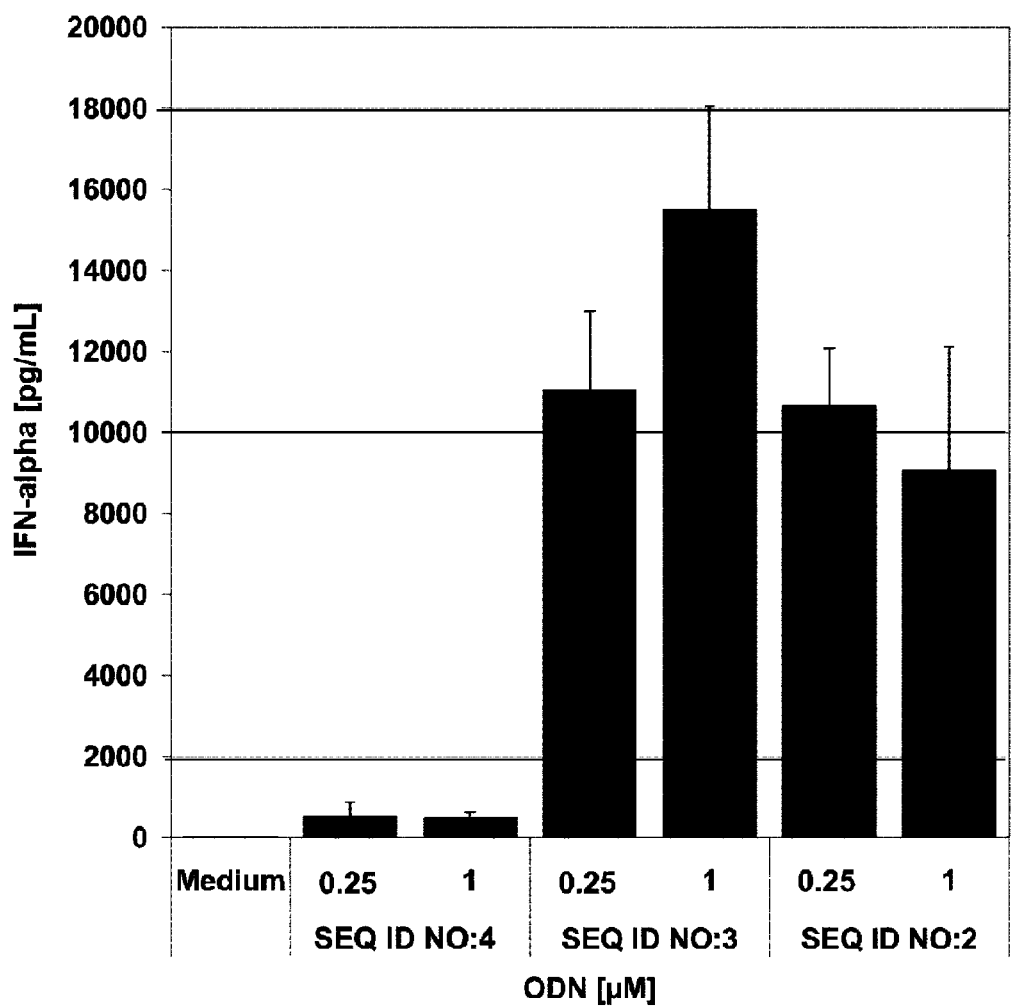
FIG. 2 is a graph depicting induction of IFN-α in isolated pDC. Magnetic isolation of pDC from peripheral blood mononuclear cells (PBMC) of two donors by CD14 depletion was followed by positive selection with BDCA-4 (Miltenyi). Data (mean+/– SEM) is shown for 24 h incubation with ODN concentrations as indicated followed by ELISA for IFN-α.
Figure 3:
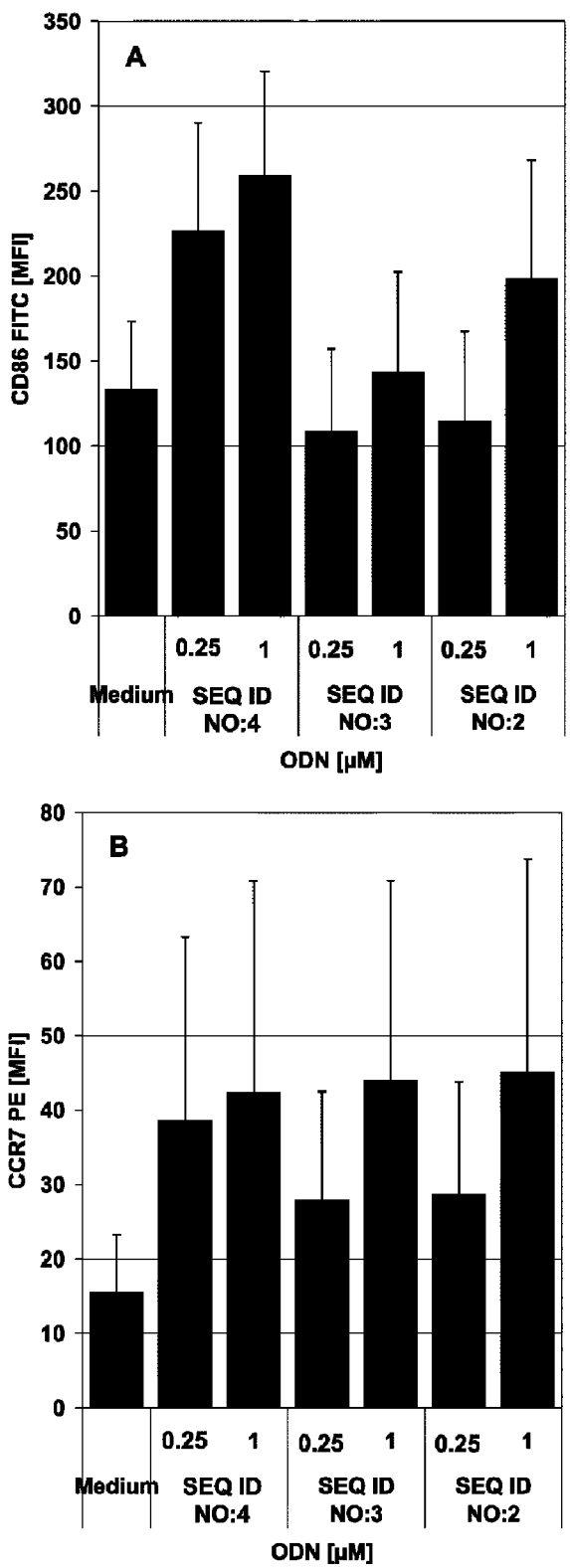
FIG. 3 is a set of graphs depicting CD86 and CCR7 in isolated pDC. Magnetic isolation of pDC from PBMC from two donors by CD14 depletion was followed by positive selection with BDCA-4 (Miltenyi). Data (mean+/– SEM) is shown for 24 h incubation with ODN concentrations as indicated followed by flow cytometric analysis of CD86 expression (FIG. 3A) (CD86 FITC, CCR-7 PE, CD14 PerCP, BDCA-4 APC) or CCR7 (FIG. 3B).
Figure 4:
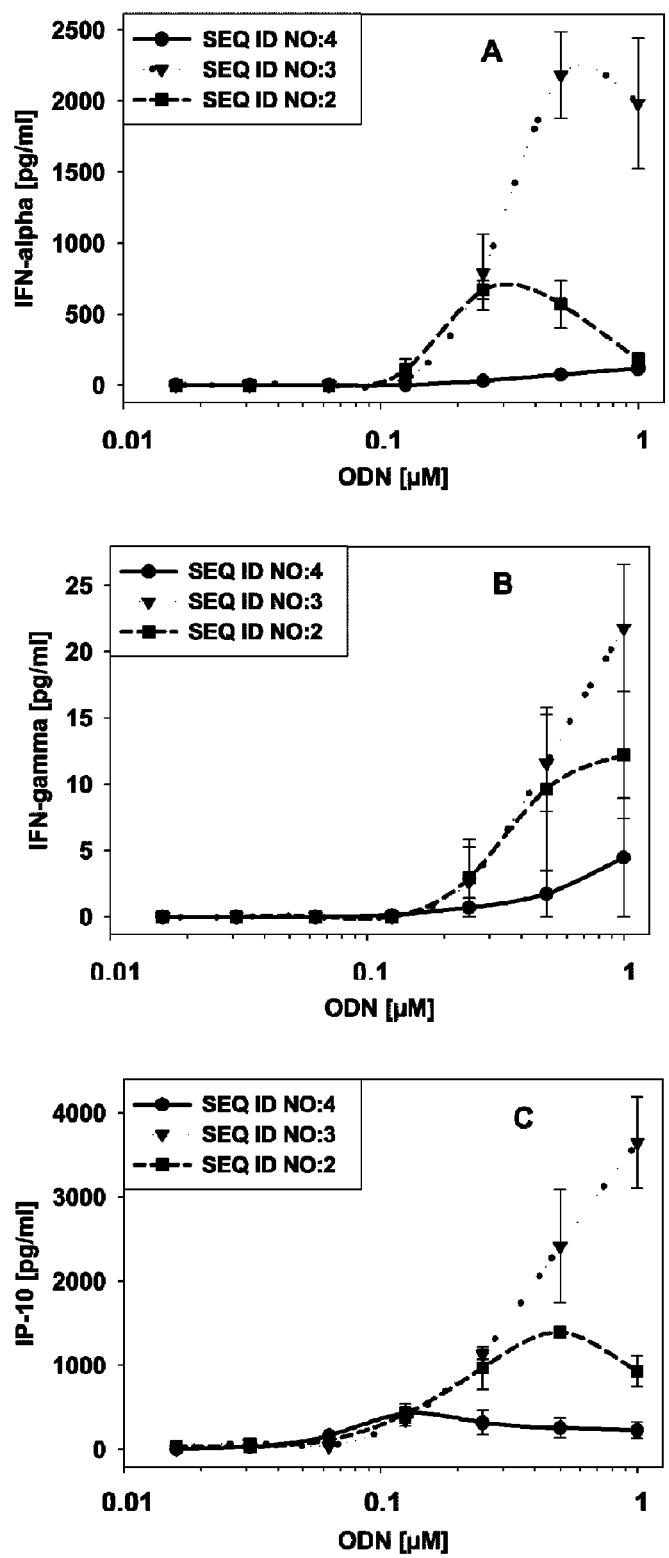
FIG. 4 is a set of graphs depicting cytokine induction in PBMC. PBMC from two donors were incubated with CpG ODN at 0.016-1 μM. After 24 h supernatants were collected and tested by 25-plex (Biosource). Shown is the mean+/– SEM of cytokines IFN-α (FIG. 4A), IFN-γ (FIG. 4B), and IP-10 (FIG. 4C) secreted by the PBMC of the two donors.
Figure 5:
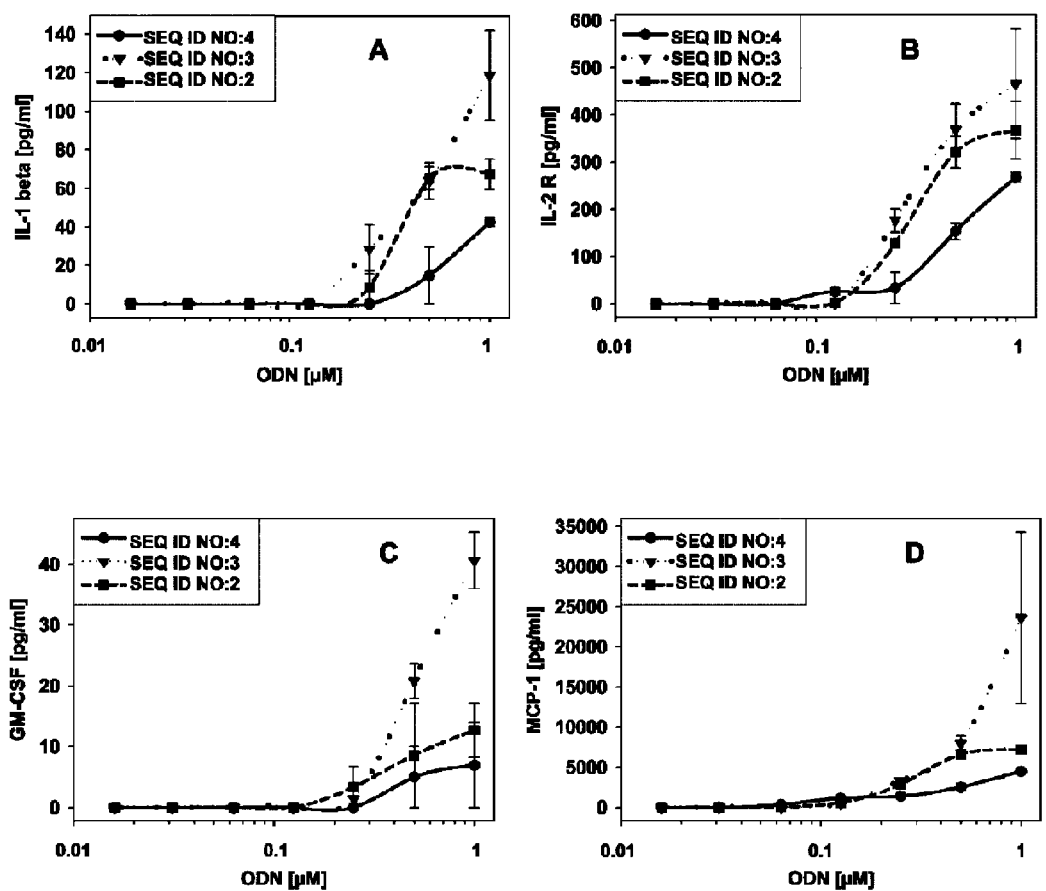
FIG. 5 is a set of graphs depicting cytokine induction in PBMC. PBMC from two donors were incubated with CpG ODN at 0.016-1 μM. After 24 h supernatants were collected and tested by 25-plex (Biosource). Shown is the mean+/– SEM of cytokines IL-1β (FIG. 5A), IL-2R (FIG. 5B), GM-CSF (FIG. 5C), and MCP-1 (FIG. 5D) secreted by the PBMC of the two donors.
Figure 6:
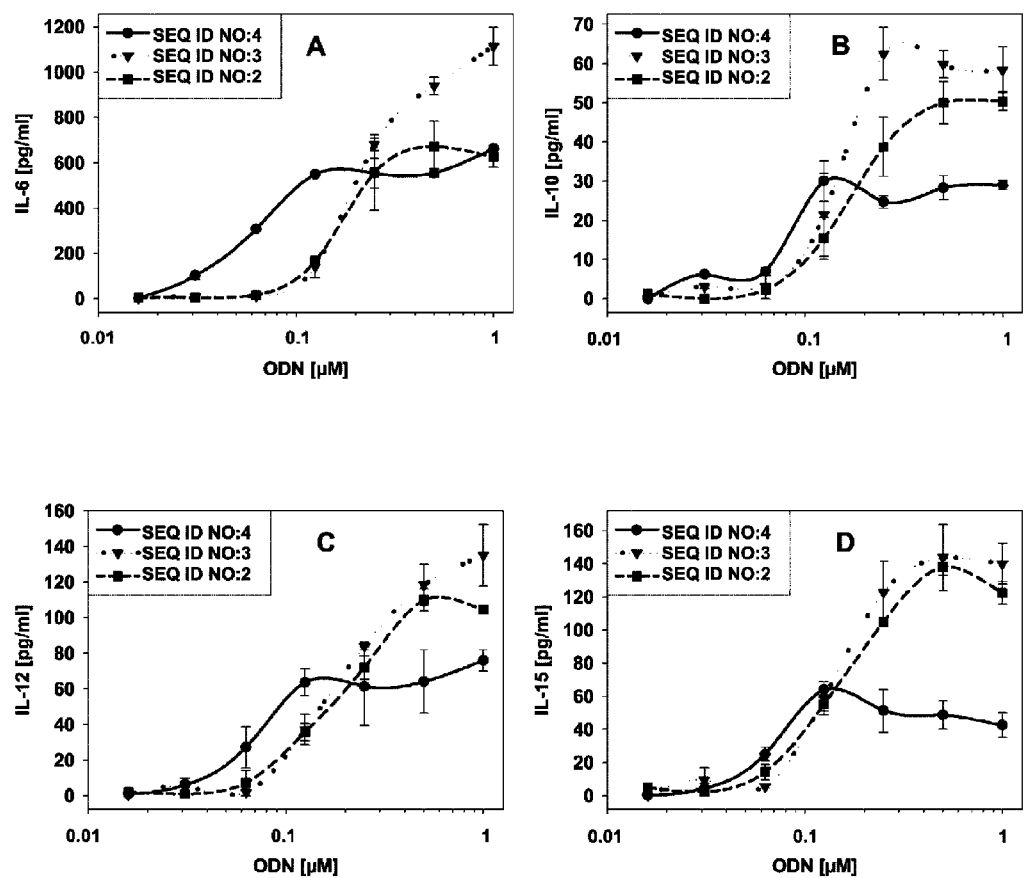
FIG. 6 is a set of graphs depicting cytokine induction in PBMC. PBMC from two donors were incubated with CpG ODN at 0.016-1 μM. After 24 h supernatants were collected and tested by 25-plex (Biosource). Shown is the mean+/– SEM of cytokines IL-6 (FIG. 6A), IL-10 (FIG. 6B), IL-12 (FIG. 6C), and IL-15 (FIG. 6D) secreted by the PBMC of the two donors.

As demonstrated in FIG. 2 and FIG. 3, the CpG oligonucleotides tested in the assays were able to activate pDC cells, as represented by the induction of IFN-α, CD86 and CCR7. As shown in FIG. 4-FIG. 7, the CpG oligonucleotides tested in the assays were able to activate PBMC, as indicated by the induction of IFN-α, IFN-γ, IP-10, IL-1β, IL2R, GM-CSF, MCP-1, IL-6, IL-10, IL-12, IL-15, MIP-1α, TNF-α, and MIP-1β. As shown in FIG. 8, the CpG oligonucleotides tested in the assays were able activate NK cells as assessed by an increase in cytotoxicity. As shown in FIG. 9, the CpG oligonucleotides tested in the assays were able to activate B cells, as indicated by B cell proliferation.

The C-class CpG ODN (SEQ ID NO: 2 and 3) showed increased potency in the assays (IFN-α, IFN-γ, IP-10, IL-1β, IL2R, GM-CSF, MCP-1, IL-10, IL-12, IL-15, and TNF-α) as compared to the B-class CpG ODN (SEQ ID NO: 4), particularly at higher doses. The C-class CpG ODN also showed an increase in NK cell activation. At approximately equivalent concentrations, exposure to the C-class CpG ODN resulted in greater cytotoxicity than exposure to the B-class CpG ODN.

Example 3

Human and Mouse TLR9 Signaling in Response to Oligonucleotides

HEK 293 cells were transfected with human and mouse TLR8 constructs to produce hTLR8-NFκB-293 cells and mTLR8-NFκB-293 cells, respectively. The cells were incubated with an ODN (SEQ ID NO: 2, 3, or 4) or with TNF-α for 16 hours. The cells were lysed and the signal was determined by luciferase readout.

The results are shown in FIG. 10. Only TNF-α stimulated significant levels of human and murine TLR8.

Example 4

Assays on Primary Mouse Cells and In Vivo

Levels of B cell proliferation and cytokine induction by splenocytes following exposure of these cells in vitro to the CpG oligonucleotides are shown in FIG. 11 and FIG. 12. As noted, above, the figures use SEQ ID NOs to refer to the specific oligonucleotides that were evaluated (SEQ ID NO: 2, 3, or 4). FIG. 11 and FIG. 12 include data for exposure of the splenocytes to a negative control (SEQ ID NO: 5), which is an ODN that has a similar nucleotide sequence as the B-class CpG ODN (SEQ ID NO: 4), except that the C-G motifs are switched to G-C motifs. The (molar) concentration of the oligonucleotide used to produce a particular data point is depicted along the X-axis (μM) of each graph.

As shown in FIG. 11, the C-class CpG ODN (SEQ ID NO: 2 and 3) induced significantly more B cell proliferation, particularly at higher concentrations, than either the B-class CpG ODN (SEQ ID NO: 4) or the negative control (SEQ ID NO: 5). As shown in FIG. 12, the CpG oligonucleotides tested in the assays were able to induce production of IFN-α, IFN-γ, and TNF-α.

Cytokine levels were also assessed in vivo in mice. Female BALB/c mice (5 per group) were injected SC with differing doses (100 mg, 250 mg or 500 mg) of CpG ODN (SEQ ID NO: 2, 3, or 4) or non-CpG control (SEQ ID NO 5). The mice were bled at 3 hr post injection and the isolated plasma was tested for IP-10 and IL-6 by ELISA.

As shown in FIG. 13, the CpG ODN induced significant levels of IP-10 and IL-6, with the C-class CpG ODN producing significantly higher levels of IP-10 than the B-class CpG ODN.

Example 5

Cellular Activation in Draining Lymph Node (LN) and PBMC Following In Vivo Administration of CpG ODN Levels of B, T, NK, myeloid dendritic cell (mDC), and pDC cell activation were assessed in draining lymph node and isolated blood. BALB/c mice (10 per group) were injected in hind footpads with 10 μg/50 μL of ODN as indicated. Placebo control group received 50 μL of PBS. Twenty four hours following administration, blood and popliteal LN were removed and pooled within groups. Isolated PBMCs (by Ficoll) and lymph node cell fractions (by magnetic activated cell sorting) were analyzed by flow cytometry for expression of cellular markers.

The results for cellular activation in draining LN and in PBMC are shown in Table 1 and Table 2, respectively, as Mean Fluorescent Intensity/% Expression.

TABLE 1

Cellular Activation in draining LN (Mean Fluorescent Intensity/% Expression)

| | mDC ($B220^-CD11b^+CD11c^{med/high}$) | | | pDC ($B220^+CD11b^{med}CD11c^{low}$) | | | B (CD19) | T (CD3) | NK (DX5) |
|---|---|---|---|---|---|---|---|---|---|
| | CD40 | CD86 | MHCII | CD40 | CD86 | MHCII | CD69 | CD69 | CD69 |
| PBS | 161/91 | 12/33 | 931 | 8/74 | 2/9 | 54/88 | 53/7 | 9/10 | 291/52 |
| SEQ ID NO: 4 | 202/99 | 51/99 | 1000 | 22/99 | 4/65 | 121/98 | 122/83 | 26/42 | 465/86 |
| SEQ ID NO: 3 | 160/95 | 78/95 | 996 | 14/98 | 6/82 | 111/96 | 140/93 | 37/63 | 532/93 |
| SEQ ID NO: 2 | 249/99 | 85/99 | 1000 | 13/99 | 5/78 | 106/97 | 139/95 | 41/73 | 533/96 |
| SEQ ID NO: 5 | 16/78 | 18/78 | 956 | 7/80 | 2/11 | 72/81 | 44/7 | 11/10 | 359/54 |

TABLE 2

Cellular Activation in PBMC (Mean Fluorescent Intensity/% Expression)

| | mDC ($B220^-CD11b^+CD11c^{med/high}$) | | | pDC ($B220^+CD11b^{med}CD11c^{low}$) | | | B (CD19) | T (CD3) | NK (DX5) |
|---|---|---|---|---|---|---|---|---|---|
| | CD40 | CD86 | MHCII | CD40 | CD86 | MHCII | CD69 | CD69 | CD69 |
| PBS | 7/97 | 6/2 | 54/95 | 10/97 | 2/5 | 50/95 | 13/8 | 8/8 | 31/36 |
| SEQ ID NO: 4 | 16/95 | 11/7 | 49/96 | 9/95 | 2/14 | 39/96 | 23/13 | 14/17 | 31/41 |
| SEQ ID NO: 3 | 15/96 | 10/8 | 95/96 | 9/96 | 2/11 | 52/96 | 22/13 | 13/15 | 36/49 |
| SEQ ID NO: 2 | 14/94 | 9/8 | 97/92 | 8/94 | 2/19 | 52/92 | 39/17 | 20/21 | 42/56 |
| SEQ ID NO: 5 | 11/96 | 7/3 | 56/94 | 9/96 | 2/6 | 48/94 | 23/11 | 13/12 | 40/45 |

Example 6

Induction of NK Cell Activity in Mouse Splenocytes by CpG ODN

BALB/c mouse splenocytes ($30 \times 10^6$) were incubated with 0 μg/mL (media alone), 1 μg/mL, 3 μg/mL or 10 μg/mL of ODN as indicated for 24 h. NK activity was evaluated using standard 51Cr-release assay with YAC-1 target cells at various effector:target ratios.

The data are shown in FIG. 14. The C-class CpG ODN (SEQ ID NO: 2 and 3) induced significant amounts of NK cell activity as measured by percent lysis at the three different concentrations.

Example 7

Treatment of Tumors In Vivo by CpG ODN

Lewis Lung Carcinoma (LLC) Survival and Tumor volume was assessed. Female C57Bl/6 mice (~20 g @ start of study; 10 per group) were used in the study. Tumor Induction was achieved by SC injection of $1 \times 10^5$ LLC cells (ATCC; CRL 1642) in the lower back of the animals. The ODN (SEQ ID NO: 2-5) were administered by SC injection (200 mg) in the tumor perimeter on day 1 and 3 and then twice weekly. Animals were monitored for tumor growth and survival. Tumor size (the length and the width) was measured using a digital vernier caliper. Tumor volume was calculated using the formula: Tumor volume=$(0.4)(ab^2)$, where a=larger diameter and b=smaller diameter. Changes in average tumor volume were assessed until 50% death in each animal group. The results are shown in FIG. 15. Mice euthanized on day of tumor measurement are not included on graphs. At 100 days post tumor induction, both C-class CpG ODN (SEQ ID NO: 2 and 3) induced higher percent survival than the other ODN.

Neuroblastoma Therapy was also assessed. Female A/J mice (~20 g @ start of study; 10 per group) were used. Tumor Induction was achieved by SC injection of $1 \times 10^6$ neuro-2a cells (ATCC; CCL 131) in the upper left flank of the mice. The ODN (SEQ ID NO: 2-5) were administered by SC injection (100 mg) in the tumor perimeter starting from day 10 post tumor injection. Mice were treated either daily or every 3rd day for 15 days and monitored for tumor growth and survival. The results are shown in FIG. 16.

Example 8

Local Reactogenicity in Guinea Pigs to Assess Safety

Local reactions of C-class CpG ODN (SEQ ID NO: 2 or 3) or B-class CpG ODN (SEQ ID NO: 4) were assessed in a "skinny" guinea pig model. Hairless IAF guinea pigs received various doses (0.3 mg, 1.0 mg or 3.0 mg) of the C-class or B-class CpG ODN. All injections were administered intradermally (ID) on the dorsal side of the guinea pig below the scapula and lateral to the spine in a fixed volume. Control animals received an ID injection of a fixed volume of PBS. The guinea pigs were monitored at regular intervals following dosing (at 6 hr, 24 hr, and every 24 hr thereafter) and edema was recorded.

Table 3 and Table 4 show mean grade of edema at various time points post dose for animals receiving the C-class CpG ODN (SEQ ID NO: 2) and the B-class CpG ODN (SEQ ID NO: 4), respectively. The tables employ the following scale to measure edema: O—no edema; I—very mild edema; barely perceptible; II—mild edema; area well-defined by raised edge; III—moderate edema; area raised by approximately 1 mm; IV—severe edema; area raised >1 mm and extending beyond area of exposure.

The C-class CpG ODN (SEQ ID NO: 2; data not shown for SEQ ID NO: 3) generally exhibited a lower degree of edema following ID injection than the B-class CpG ODN (SEQ ID NO: 4).

TABLE 3

Edema following administration of C-class ODN (SEQ ID NO: 2)

| Time | Dose (mg) | | | | | | | | | | | | | |
|---|---|---|---|---|---|---|---|---|---|---|---|---|---|---|
| | 3.0 | | | | | 1.0 | | | | | 0.3 | | | |
| (h) | 1 | 2 | 3 | 4 | 5 | 1 | 2 | 3 | 4 | 5 | 1 | 2 | 3 | 4 |
| 6 | O | O | I | I | II | I | I | I | I | I | I | O/I | I | I |
| 24 | I | O | O | O | I | I | I | I | I | I | I | O | I | O/ |
| 48 | O | O | O | I | O | O | I | I | I | I | O | O | O | O |
| 72 | O | O | O | O | O | O | O | O | O | O | O | O | O | O |
| 96 | O | O | O | O | O | O | O | O | O | O | O | O | O | O |
| 120 | O | O | O | O | O | O | O | O | O | O | O | O | O | O |

TABLE 4

Edema following administration of B-class ODN (SEQ ID NO: 4)

| Time | Dose (mg) | | | | | | | | | | | | | | |
|---|---|---|---|---|---|---|---|---|---|---|---|---|---|---|---|
| | 3.0 | | | | | 1.0 | | | | | 0.3 | | | | |
| (h) | 1 | 2 | 3 | 4 | 5 | 1 | 2 | 3 | 4 | 5 | 1 | 2 | 3 | 4 | 5 |
| 6 | O | O | I | I | II | I | I | I | II | II | III | I | I | II | II |
| 24 | II | II | II | II | II | II | I | II | II | II | II | I | I | II | I |
| 48 | I | I | I | II | II | I | I | I | I | I | O | I | I | I |
| 72 | O | O | I | I | II | O | O | O | O | O | O | O | O/I | I | I |
| 96 | O | O | O | O | O | O | O | O | O | O | O | O | O | O | I |
| 120 | O | O | O | O | O | O | O | O | O | O | O | O | O | O | O |

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention, in addition to those shown and described herein, will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. An immunostimulatory oligonucleotide having a base sequence comprising 5' TCGTCGTTTTCGGCGCGCGC-CGT 3' (SEQ ID NO: 1), wherein each C is unmethylated and the oligonucleotide is 23-26 nucleotides in length.

* * * * *

UNITED STATES PATENT AND TRADEMARK OFFICE
CERTIFICATE OF CORRECTION

| | | |
|---|---|---|
| PATENT NO. | : 8,198,251 B2 | Page 1 of 1 |
| APPLICATION NO. | : 12/190402 | |
| DATED | : June 12, 2012 | |
| INVENTOR(S) | : Vollmer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 453 days.

Signed and Sealed this
Thirteenth Day of November, 2012

David J. Kappos
*Director of the United States Patent and Trademark Office*